(12) United States Patent
Abdi et al.

(10) Patent No.: US 9,542,641 B2
(45) Date of Patent: Jan. 10, 2017

(54) SYSTEMS AND METHODS FOR FAULT DIAGNOSIS IN MOLECULAR NETWORKS

(76) Inventors: Ali Abdi, Short Hills, NJ (US); Effat S. Emamian, Newark, NJ (US)

(*) Notice: Subject to any disclaimer, the term of this patent is extended or adjusted under 35 U.S.C. 154(b) by 1373 days.

(21) Appl. No.: 13/006,901

(22) Filed: Jan. 14, 2011

(65) Prior Publication Data

US 2011/0202283 A1    Aug. 18, 2011

Related U.S. Application Data

(63) Continuation of application No. 12/527,269, filed as application No. PCT/US2008/054674 on Feb. 22, 2008, now abandoned.

(60) Provisional application No. 60/902,767, filed on Feb. 22, 2007.

(51) Int. Cl.
| | |
|---|---|
| *G06F 19/00* | (2011.01) |
| *G06N 3/00* | (2006.01) |
| *B82Y 10/00* | (2011.01) |
| *G06F 19/12* | (2011.01) |

(52) U.S. Cl.
CPC ............ *G06N 3/002* (2013.01); *B82Y 10/00* (2013.01); *G06F 19/12* (2013.01)

(58) Field of Classification Search
CPC .......... B82Y 10/00; G06N 3/002; G06F 19/12
USPC .......................................................... 702/19
See application file for complete search history.

(56) References Cited

U.S. PATENT DOCUMENTS

| | | | | |
|---|---|---|---|---|
| 8,594,941 | B2* | 11/2013 | Chandra et al. | 702/19 |
| 2003/0104475 | A1* | 6/2003 | Kelly et al. | 435/7.1 |
| 2006/0051838 | A1* | 3/2006 | Hwa et al. | 435/69.1 |
| 2008/0261820 | A1* | 10/2008 | Iyengar et al. | 506/8 |

OTHER PUBLICATIONS

Asadi et al., "Soft Error Modeling and pRotection for Sequential Elements," IEEE International Symposium on Defect and Fault Tolerance of VLSI Systems (2005): pp. 463-474.
Asadi et al., "An Analytical Approach for Soft Error Rate Estimation in Digital Circuits," IEEE International Conference on Circuits and Systems (2005):pp. 2991-2994.

(Continued)

*Primary Examiner* — Sujoy Kundu
*Assistant Examiner* — Ricky Ngon
(74) *Attorney, Agent, or Firm* — Fox Rothschild LLP

(57) ABSTRACT

The present disclosure provides advantageous systems and methods for identifying molecular vulnerabilities in biological pathways and networks. The present disclosure generally involves conceptualizing a disease/disorder at the molecular level as a faulty physiological system, wherein one or more molecules in the complex intracellular signaling network are dysfunctional. This is accomplished by modeling a given physiological system as a digital logic circuit. More particularly, in exemplarily embodiments, binary logic equations are derived by analyzing the interactions between the input and output nodes of a target biological system. These equations are then used to produce a digital circuit representation for the system. Once a digital circuit representation is created, this circuit may advantageously be analyzed, using fault analysis techniques, in order to determine the vulnerability levels of the molecules of the targeted system.

55 Claims, 25 Drawing Sheets

(56) References Cited

OTHER PUBLICATIONS

Asadi et al., "An Accurate SER Estimation Method Based on Propagation Probability," IEEE Design and Test Automation in Europe (2005): pp. 306-307.
Blain et al, "Breast cancer banishes p27 from nucleus," Nature Medicine (Oct. 2002); 8(10):1076-1078.
Boronenkov et al., "The sequence of phophatidylinositol-4-phosphate 5-kinase defines a novel family of lipid kinases," The Journal of Biological Chemistry (Feb. 17, 1995): 270(7):2881-2884.
Brazil et al., "Advances in protein kinase B signalling: AKTion on multiple fronts," Trends in Biochemical sciences (May 2004); 29(5):233-242.
Cardone et al., "Regulation fo Cell Death Protease Caspase-9 by Phosphorylation," Science (Nov. 13, 1998): vol. 282, pp. 1318-1321.
Colin et al., "Akt is altered in an animal model of Huntington's disease and in patients," European Journal of Neuroscience (2005): vol. 21, pp. 1478-1488.
Chen et al., "Interaction of Akt-Phosphorylated Ataxin-1 with 14-3-3 Mediates Neurodegeneration in Spinocerebellar Ataxia Type 1," Cell (May 16, 2003): vol. 113, pp: 457-468.
DeVivo et al., "Characterization of the 5-Hydroxytryptamine1A Receptor-Mediated Inhibition of Forskolin-Stimulated Adenylate Cyclase Activity in Guinea Pig and Rat Hippocampal Membranes1," The Journal of Phamaclology and Experimental Therapeutics (1986):238(1):248-253.
Delcommenne et al., "Phophoinositide-3-0H kinase-dependent regulation of glycogen synthase kinase 3 and protein kinase B/AKT by the integrin-linked kinase," Proc. Natl. Acad. Sci. (Sep. 1998): vol. 95, pp. 11211-11216.
Emamian et al., "Serine 776 of Ataxin-1 Is Criticial for Polyglutamine-Induced Disease ni SCA1 Transgenic Mice," Neron (May 8, 2003): vol. 38, pp. 375-387.
Emamian et al., "Convergent evidence for impaired AKT1-GSK3β signaling in schizophrenia," Nature Genetics (Feb. 2004):36(2)131-137.
Griffin et al., "Activation of Akt/PKB, increased phophorylation of Akt substrates and loss and latered distribution of Akt and PTEN are features of Alzheimer's disease pathology," Journal of Neurochemistry (2005); vol. 93, pp. 105-117.
Janes et al., "The Response of Human Epithelial Cells to TNF Involves and Inducible Autocrine Cascade," Cell (Mar. 24, 2006): vol. 124, pp. 1225-1239.
Janes et al., "A High-throughput Quantitative Multiplex Kinase Assay for Monitoring Information Flow in Signaling Networks," Molecular & Cellular Proteomics 2.7, pp. 463-473.
Eric R. Kandel, "The Molecular biology of Memory Storage: A dialogue Between Genes and Synapses," Science (Nov. 2, 2001): vol. 294, pp. 1030-1038.
Kaspar et al., "Retrograde Viral Delivery of IGF-1 Prolongs Survival in a Mouse ALS Model," Science (Aug. 8, 2003): vol. 301, pp. 839-842.
Levine et al., "The P53 pathway: what questions remain to be explored?," Cell Death and Differentiation (2006): vol. 13, pp. 1027-1036.
Liang et al., "PKB/Akt phophorylates p27, impairs nuclear import of p27 and opposes p27-mediated G1 arrest," Nature Medicine (Oct. 2002): 8(10):1153-1160.
Luo et al., "Targeting the PI3K-Akt pathway in human cancer: Rationale and promise," Cancer Cell (Oct. 2003): vol. 4, pp. 257-262.
Ma'ayan et al., "FOrmation of Regulatory Patterns During Signal Propagation in a Mammalian Cellular Network," Science (Aug. 12, 2005): vol. 309, pp. 1078-1083.
Papin et al., "Reconstruction of Cellular Signalling Networks and Analysis of Their Properties," Nature Reviews (Feb. 2005): vol. 6, pp. 99-111.
Saez-Rodriguez et al., "Modular Analysis of Signal Transduction Networks," IEEE Control Systems Magazine (Aug. 2004):pp. 35-52.
Saudou et al., "Huntingin Acts in the Nucleus to Induce Apoptosis but Death Does Not Correlate with the FOrmation fo Intranuclear Inclusions," Cell (Oct. 2, 1998): vol. 95, pp. 55-66.
Waard et al., "Direct binding of G-protein βg complex to voltage-dependent calcium channels," Nature (Jan. 30, 1997): vol. 385, pp. 446-450.
Ideker et al., "Building with a scaffold: emerging strategies for high-to low-level cellular modeling," Trends in Biotechnology (Jun. 2003): 21(6):255-262.
Asadi et al., "Vulnerabilty Analyis of L2 Cache Elements to Single Event Upsets", Department of Electrical and Computer Engineering, Northeastern University.
de Silva et al., "Molecular Scale Logic Gates", Chem. Eur. J. 2004, 10, 574-586.
Huang et al., "Design and Characterization of an And-Or Inverter (AOI) Gate for QCA implementation", Department of Electrical and Computer Engineering, Northeastern University, 2004.
Kitano, Hiroaki; " blogical Robustness", Nature Publishing Group, 2004, vol. 4, pp. 826-837.
Tahoori et al., "Defect arid Fault Tolerance of Reconfigurabie Molecuiar Computing" Proceedings of the 12th Annual IEEE Symposium, FCCM '04.
Tahoori et al., "Testing of Quantum Cellular Automata", IEEE Transactions on Nanotechnology, vol. 3, No. 4, Dec. 2004.
Tempesti et al., "A robust multiplexer-based FPGA inspired by biological systems", J. of Systems Architecture 43, (1997), 719-733.
DeWaard et al. "Direct binding of G-protein complex to voltage-dependent calcium channels", Nature, Vol, 385, Jan. 30, 1997, pp. 446-450.
International Search Report, PCT/US2008/054674 filed Feb. 22, 2008.

\* cited by examiner

| EGF | INSULIN | TNF | FKHR | CASPASE3 | CASPASE3 (AKT IS STUCK AT 1) |
|---|---|---|---|---|---|
| 0 | 0 | 0 | 0 | 0 | 0 |
| 0 | 0 | 1 | 0 | 1 | 0 |
| 0 | 1 | 0 | 1 | 0 | 0 |
| 0 | 1 | 1 | 1 | 0 | 0 |
| 1 | 0 | 0 | 1 | 0 | 0 |
| 1 | 0 | 1 | 1 | 0 | 0 |
| 1 | 1 | 0 | 1 | 0 | 0 |
| 1 | 1 | 1 | 1 | 0 | 0 |

FIG. 1E

| NODE | VUL. (WITH FKHR) | VUL. (WITHOUT FKHR) |
|---|---|---|
| CASPASE3 | 1 | 1 |
| FKHR | 1 | – |
| AKT | 1 | 0.874 |
| EGF | 0.5 | 0.249 |
| EGFR | 0.5 | 0.249 |
| Insulin | 0.49 | 0.245 |
| MEKK1ASK1 | 0.249 | 0.249 |
| TNF | 0.249 | 0.249 |
| ComplexI | 0.125 | 0.125 |
| ComplexII | 0.125 | 0.125 |
| ERK | 0.125 | 0.125 |
| IRS1 | 0.125 | 0.125 |
| JNK1 | 0.125 | 0.125 |
| MEK | 0.125 | 0.125 |
| MK2 | 0.125 | 0.125 |
| MKK3 | 0.125 | 0.125 |
| MKK7 | 0.125 | 0.125 |
| CASPASE8 | 0.125 | 0.125 |
| p38 | 0.125 | 0.125 |
| IKK | 0 | 0 |
| NFKB | 0 | 0 |
| cFLIPL | 0 | 0 |

FIG. 1F

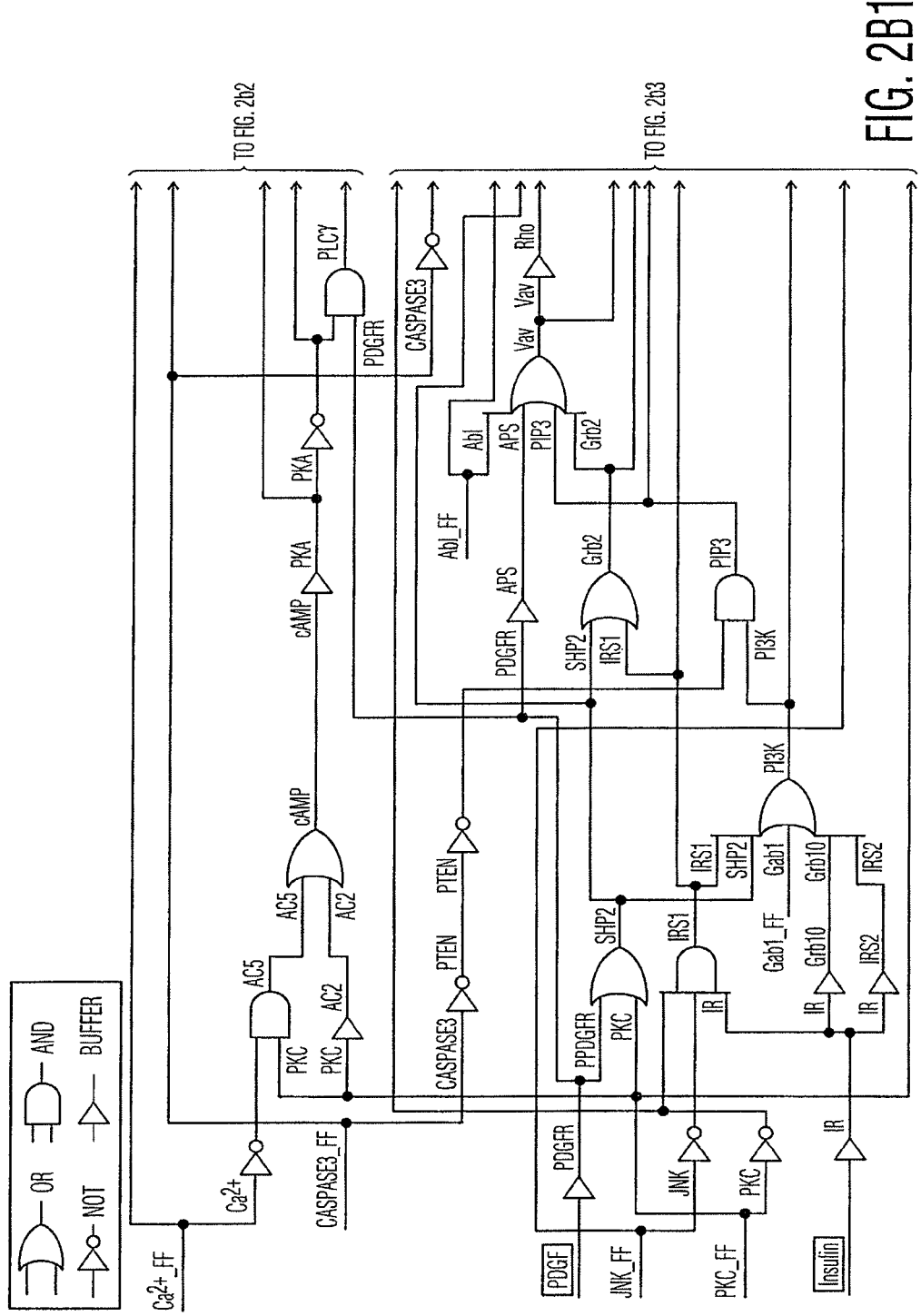
FIG. 2B1

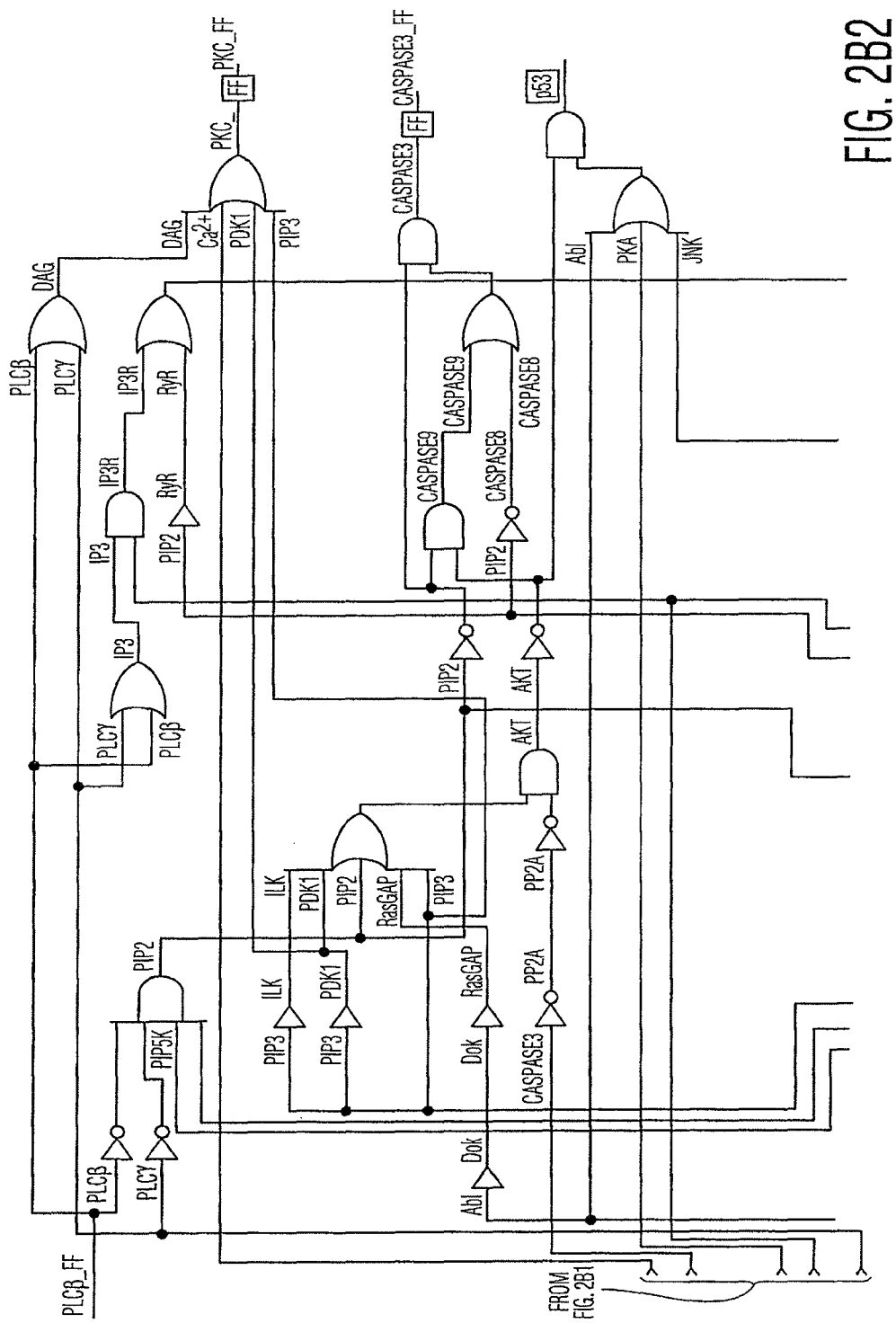

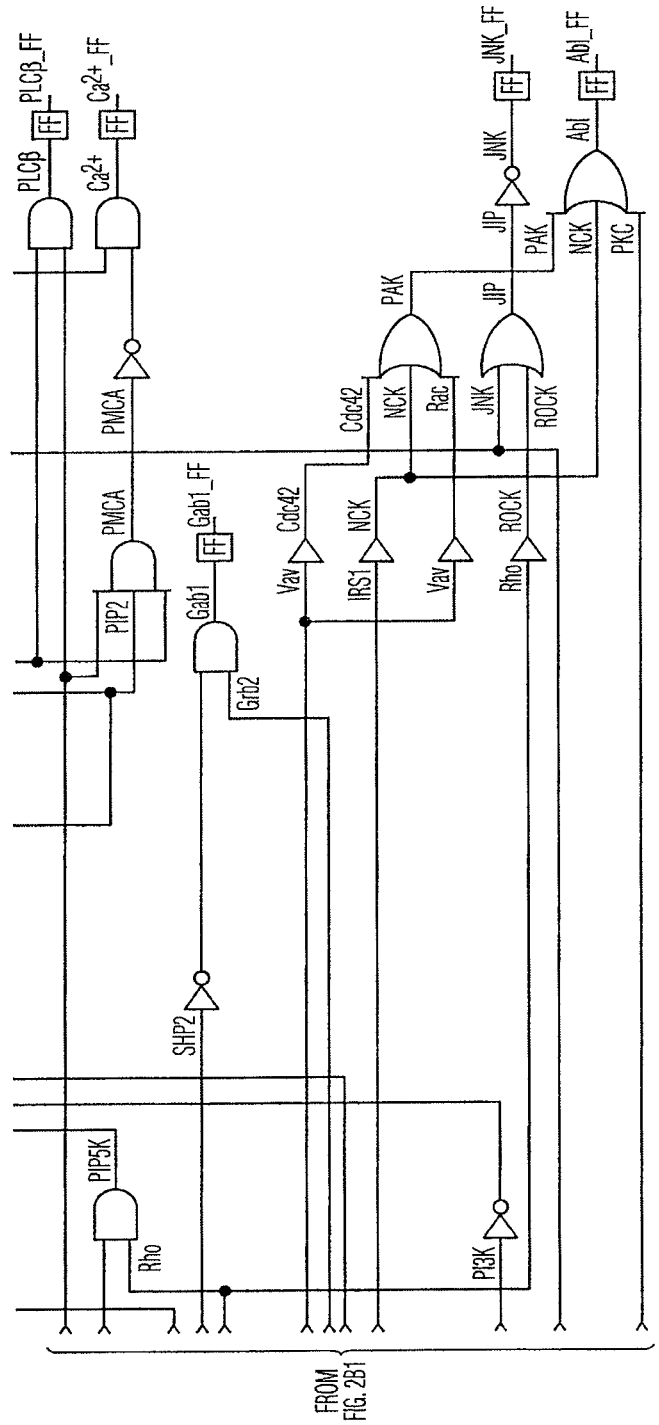
FIG. 2B3

| NODE | VUL. | NODE | VUL. | NODE | VUL. |
|---|---|---|---|---|---|
| p53 | 1 | Dok | 0.067 | ROCK | 0.022 |
| PIP2 | 0.88 | RasGAP | 0.067 | IRS1 | 0.021 |
| AKT | 0.88 | AC2 | 0.064 | Gab1 | 0.019 |
| CASPASE3 | 0.87 | ILK | 0.062 | RyR | 0.018 |
| PP2A | 0.64 | Vav | 0.061 | PDGF | 0.017 |
| CASPASE8 | 0.43 | PLCβ | 0.05 | PDGFR | 0.017 |
| PI3K | 0.35 | Ca2+ | 0.046 | IP3 | 0.015 |
| Abl | 0.29 | AC5 | 0.042 | DAG | 0.013 |
| PIP3 | 0.23 | Rho | 0.038 | PMCA | 0.011 |
| PTEN | 0.23 | Grb10 | 0.036 | CASPASE9 | 0.007 |
| PKC | 0.12 | IRS2 | 0.036 | Grb2 | 0.0052 |
| cAMP | 0.086 | PLCγ | 0.033 | Cdc42 | 0.0015 |
| PKA | 0.086 | PIP5K | 0.032 | Rac | 0.0015 |
| Insulin | 0.082 | IP3R | 0.029 | APS | 0.00025 |
| IR | 0.082 | PAK | 0.026 | NCK | 0.00012 |
| SHP2 | 0.073 | JNK | 0.023 | | |
| PDK1 | 0.071 | JIP | 0.023 | | |

FIG. 2C

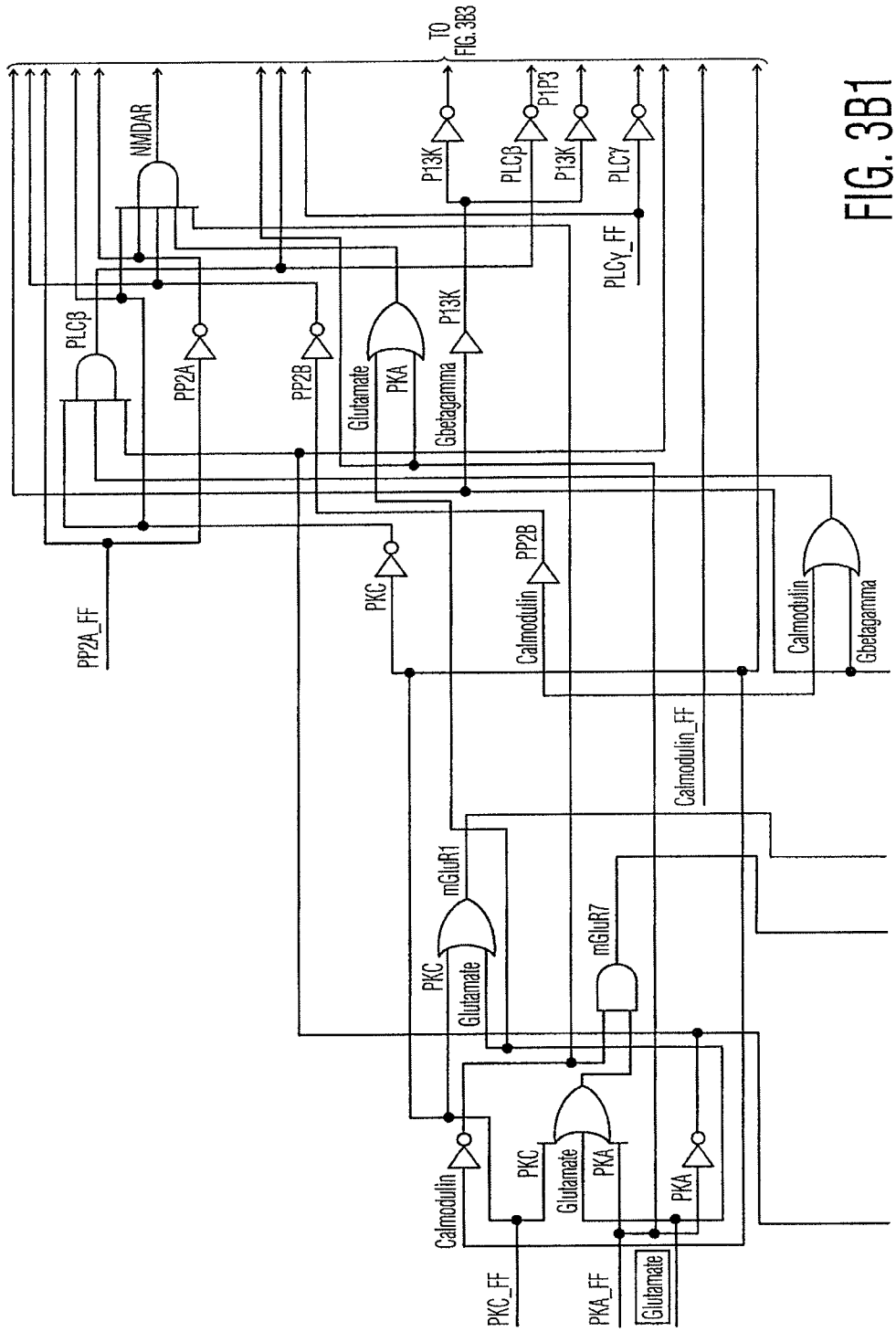
FIG. 3B1

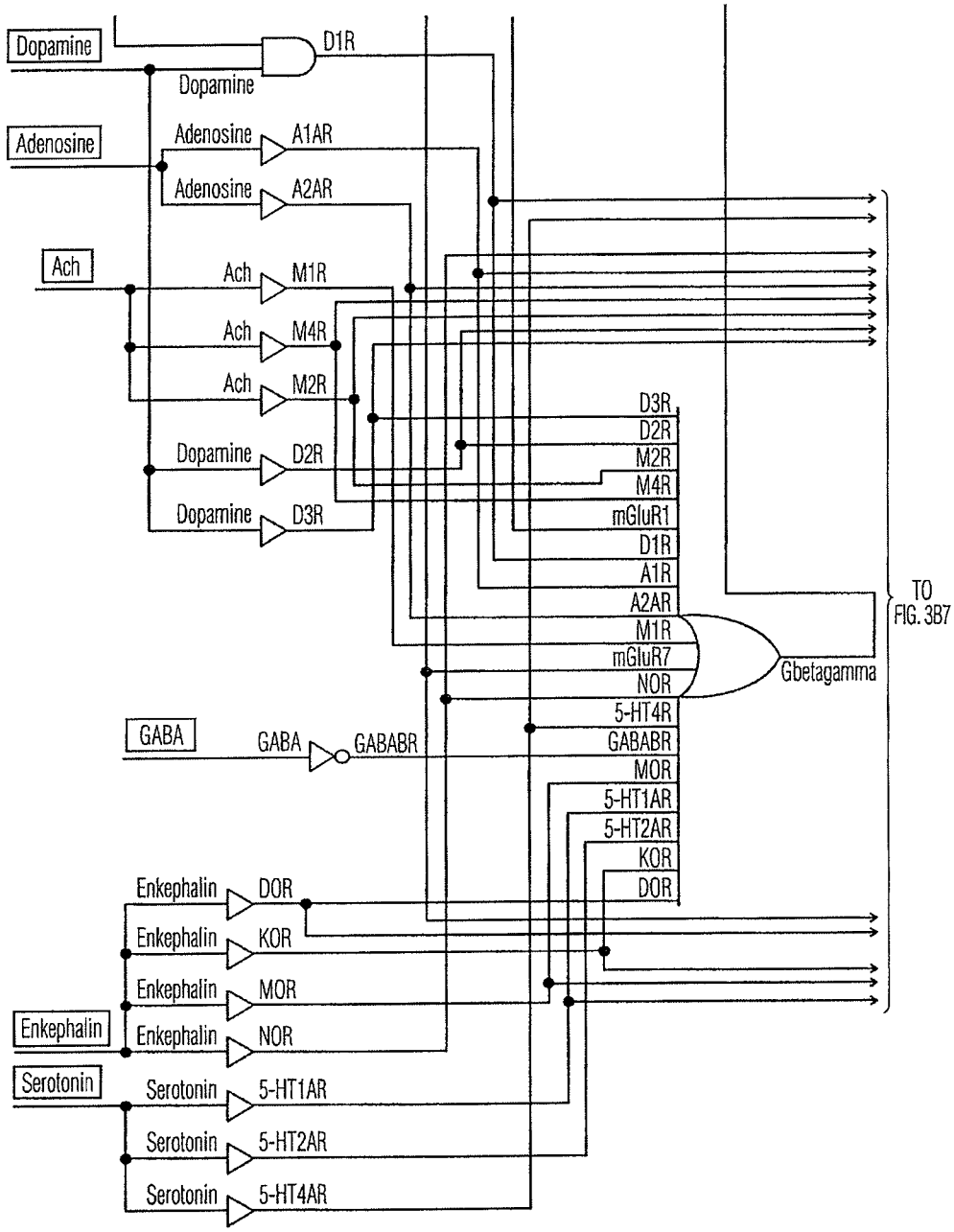
FIG. 3B2

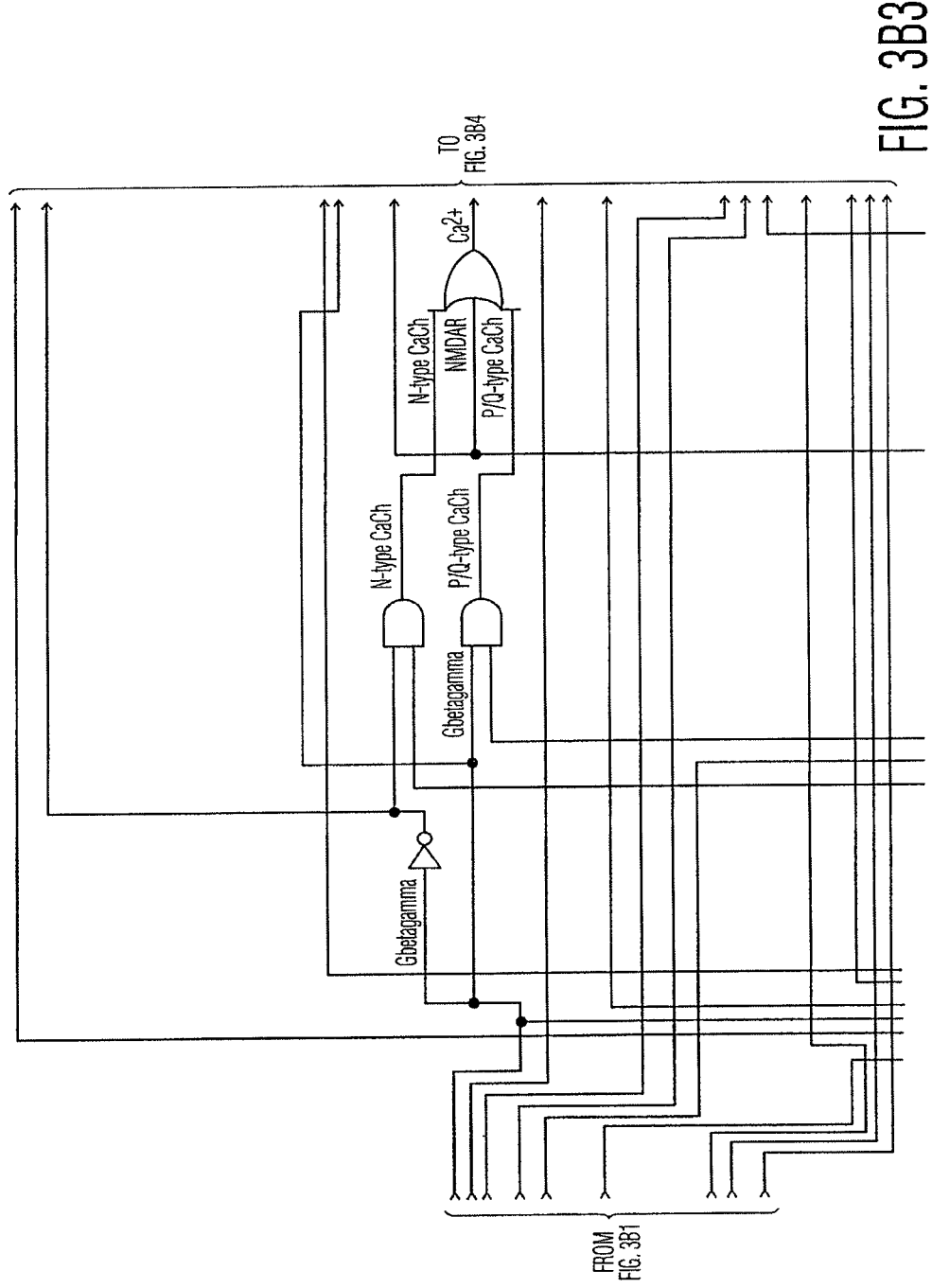

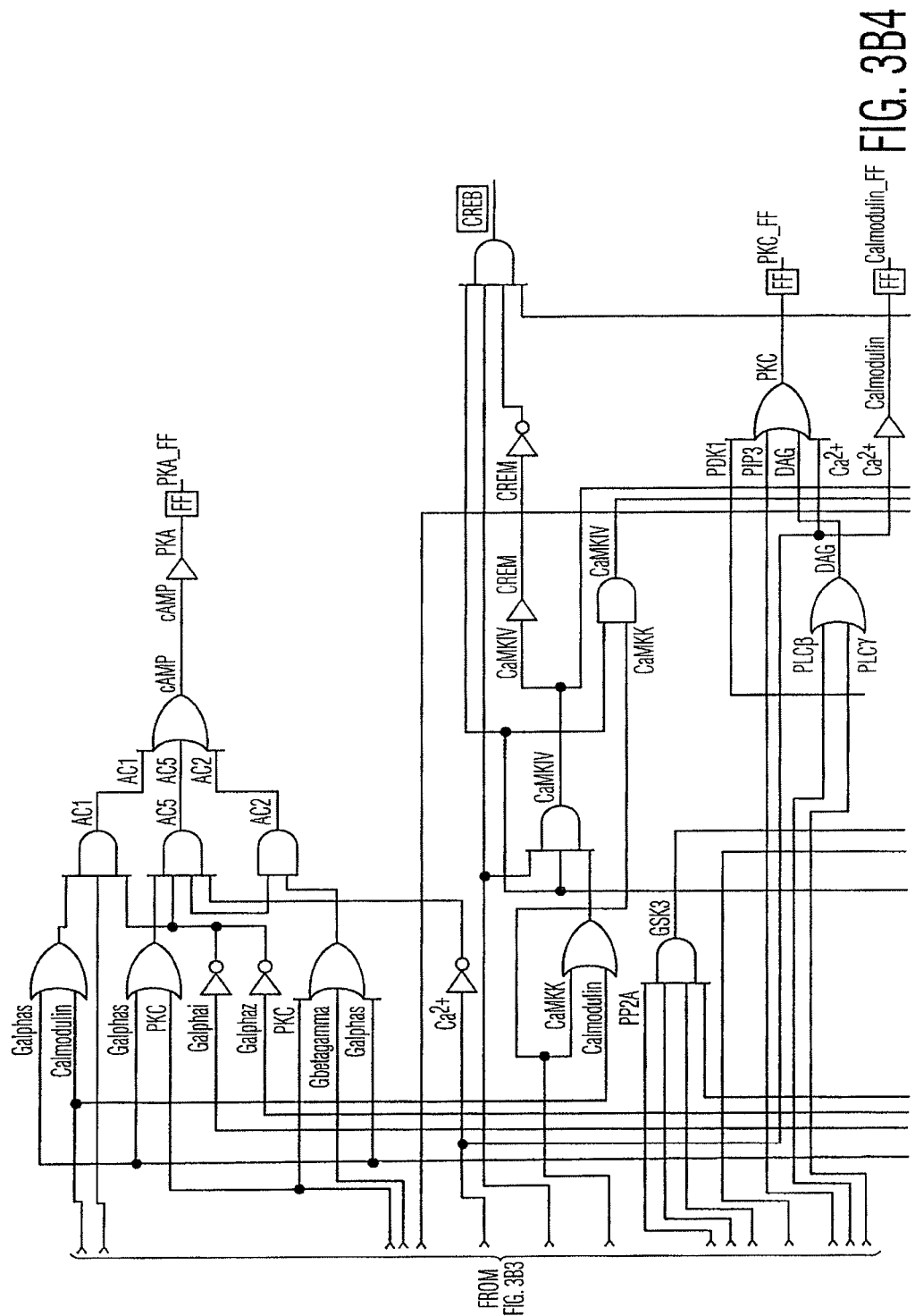
FIG. 3B4

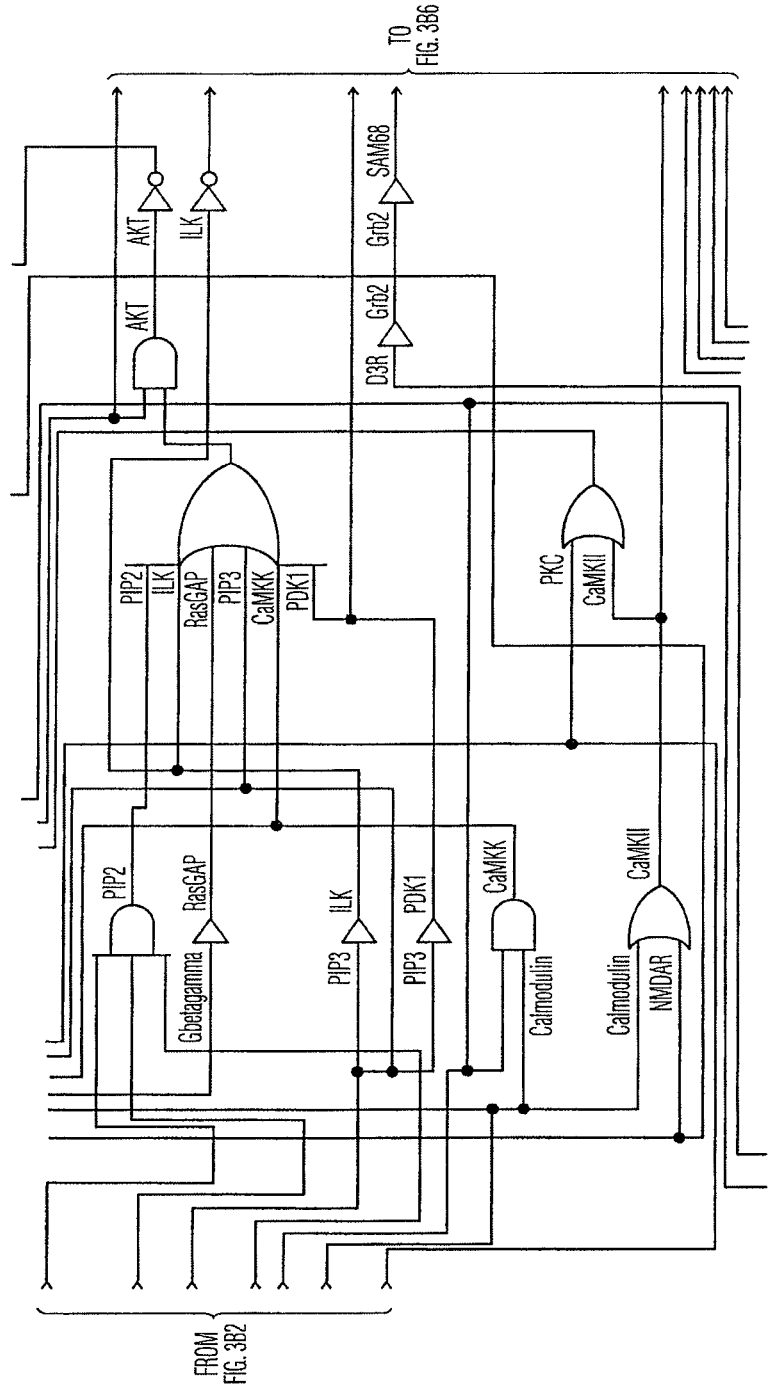
FIG. 3B5

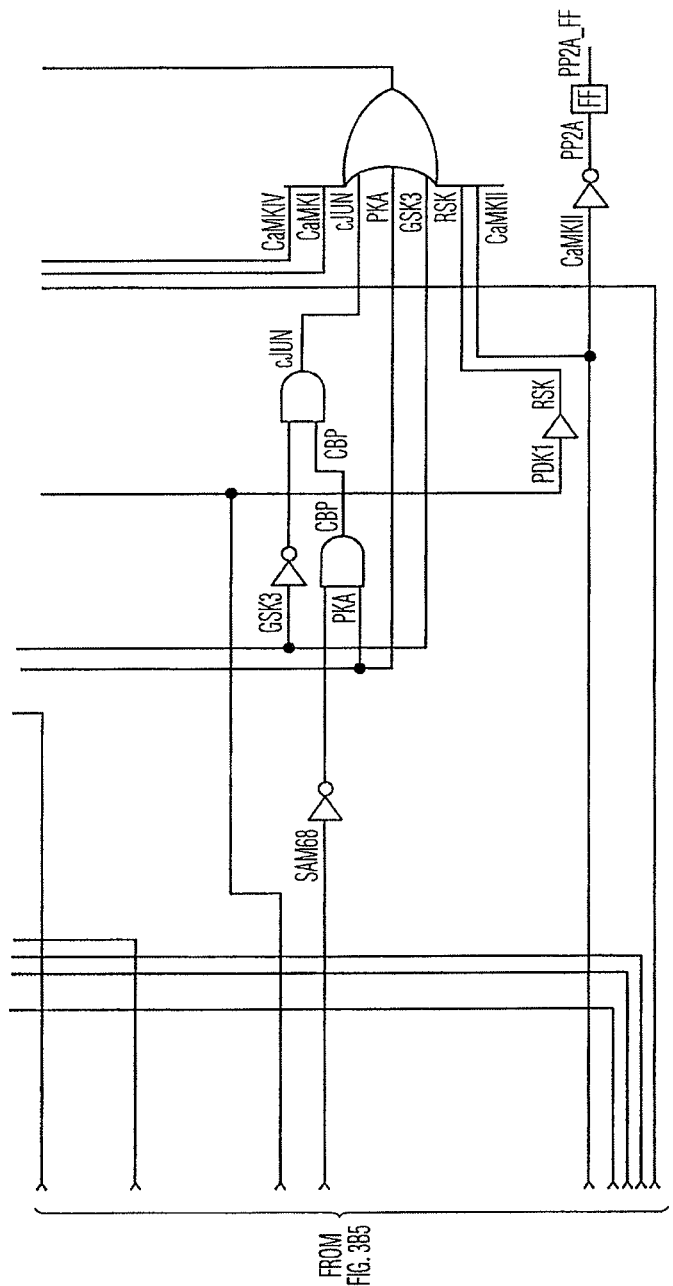
FIG. 3B6

FIG. 3B7

| NODE | VUL. | NODE | VUL. | NODE | VUL. |
|---|---|---|---|---|---|
| CREB | 1 | RSK | 0.12 | A2AR | 0 |
| Calmodulin | 0.74 | Adenosine | 0.05 | CaMKI | 0 |
| CA$^{2+}$ | 0.6 | Serotonin | 0.05 | CBP | 0 |
| cAMP | 0.59 | 5-HT1AR | 0.05 | cJun | 0 |
| Galphai | 0.58 | A1R | 0.045 | DAG | 0 |
| AC2 | 0.58 | Dopamine | 0.04 | 5-HT2AR | 0 |
| AC1 | 0.57 | Ach | 0.035 | 5-HT4R | 0 |
| AC5 | 0.57 | Enkephalin | 0.035 | GABABR | 0 |
| PKA | 0.5 | mGluR7 | 0.035 | Galphas | 0 |
| P/Q type CaCh | 0.5 | D1R | 0.025 | Grb2 | 0 |
| PP2A | 0.5 | D2R | 0.025 | GSK3 | 0 |
| Gbetagamma | 0.43 | D3R | 0.025 | ILK | 0 |
| CaMKII | 0.43 | DOR | 0.025 | M1R | 0 |
| PP2B | 0.27 | KOR | 0.025 | PIP2 | 0 |
| CaMKIV | 0.27 | M2R | 0.025 | AKT | 0 |
| CaMKK | 0.27 | M4R | 0.025 | PKC | 0 |
| CREM | 0.27 | MOR | 0.025 | PLCβ | 0 |
| N-type CaCh | 0.25 | NOR | 0.025 | PLCγ | 0 |
| NMDAR | 0.24 | Galphaz | 0.02 | RasGAP | 0 |
| P13K | 0.12 | Glutamate | 0.01 | SAM68 | 0 |
| PIP3 | 0.12 | mGluR1 | 0.01 | | |
| PDK1 | 0.12 | GABA | 0 | | |

FIG. 4A

SYSTEMS AND METHODS FOR FAULT DIAGNOSIS IN MOLECULAR NETWORKS

BACKGROUND

1. Technical Field

The present disclosure generally relates to the field of molecular biology medicine. More particularly, the present disclosure relates to systems and methods for studying biological networks and for computing molecular vulnerabilities in connection with such networks and pathways. The present disclosure implicates a wide range of applications including, but not limited to, drug research/development, disease diagnosis, gene therapy, and the like.

2. Background Art

Over the past few decades, a large amount of information has been collected regarding the function of individual signaling and other types of molecules. Many detailed individual molecular mechanisms are now known which regulate cellular function. In recent years, system biologists have started to integrate these individual interactions and components, and to analyze the properties and functions that emerge from these complex biological systems (The News Staff, 2005).

Each cell in the human body includes many biomolecules which interact with each other through an extensive network of cellular pathways. (Papin et al., 2005; Klipp et al, 2005; Gomperts et al., 2002) Accordingly, dysfunction of any such biomolecules may interfere with the efficacy and efficiency of signal transduction within the network. Such dysfunction may consequently result in a cell transitioning from a normal state of cellular function (physiological condition) to a diseased state (pathological condition). (Finkel and Gutkind, 2003)

In the case of some hereditary human diseases, such as ataxia, anemia, chorea, Huntington's disease, neurofibromatosis, polycystic kidney disease, etc., a single isolated gene is known to instigate development of the pathology. However, in the case of some of the most prevalent and incurable human diseases, such as neurodegenerative/psychiatric brain disorders and cancer, the pathology can not be linked to a single gene. In such complex trait disorders, it is not clear which molecules have causative effects, and how much each molecule may contribute to the development of the pathology. Thus, in such disorders, the main cause of pathology is typically unknown or poorly understood, thus hindering and complicating diagnosis/treatment of the pathology.

On the other hand, the disease possibly results from the dysfunction of several molecules of different pathways. Therefore, studying such pathways and, more particularly, identifying and isolating those molecular components with the greatest ability to disrupt such pathways, may advantageously provide valuable insights into the development of a disorder and possible treatment options.

Despite efforts to date, a need remains for effective and reliable systems and methods for identifying molecular vulnerabilities in relation to known biological pathways. Such systems and methods—if developed—would necessarily implicate a wide range of applications, e.g., relating to both disease diagnosis and treatment. More specifically, systems and methods are needed which advantageously model biological pathways, e.g., as digital logic circuits, and then use such models to pinpoint molecules most likely to adversely effect cellular pathways and to thereby cause disease. These and other needs are satisfied by the systems and methods disclosed herein.

SUMMARY

The present disclosure provides advantageous systems and methods for identifying molecular vulnerabilities in biological pathways. The present disclosure generally involves conceptualizing a disease/disorder at the molecular level as a faulty physiological system, wherein one or more molecules in the complex intracellular network are dysfunctional. Recent progress in genome- and proteome-wide expression analysis of biological systems provides a valuable picture of "expression levels" of molecules. In the disclosed systems and methods, it is the "functionality" of each molecule which determines the overall performance of the molecular system. Thus, molecular fault models—similar to some fault models used in digital circuits—are developed according to the present disclosure in order to quantify the functionality and dysfunctionality of different molecules in a network.

Thus, the disclosed conceptualization is accomplished by modeling a given physiological system as a digital logic circuit. More particularly, in exemplary embodiments, binary logic equations are derived by analyzing the interactions between the input and output nodes of a biological system of interest. These equations are then used to produce a digital circuit representation for the system. Once a digital circuit representation is created, this model may advantageously be analyzed, in order to determine molecular vulnerabilities.

In order to determine the molecules of greatest vulnerability, fault diagnosis techniques, e.g., vulnerability assessment methods disclosed herein, are used. Such vulnerability assessment methods provide numerical representations of the functional vulnerability for the entire molecular system as it relates to each individual molecule. Thus, a high vulnerability value for a molecule indicates a high probability that dysfunction of said molecule will disrupt the system and thereby change the system from a physiological state to a pathological state. Identification and isolation of such molecules, e.g., having high vulnerability levels, is a major step towards understating the molecular source(s) of a variety of diseases. From a drug development perspective, vulnerability assessment provides and/or helps to define/identify a set of candidate molecules to target for regulation.

Exemplary methods disclosed herein generally include the following steps:

1. Specifying initial input node(s) (such as ligands, receptors, secondary messengers, etc.) and the final output node(s) (such as different transcription factors relevant to the input signal), as well as the intermediate molecules relevant to signal propagation for a network of interest.
2. Identifying types of interactions (e.g., stimulatory or inhibitory) between the molecules, e.g., using known interactions disclosed in the technical literature.
3. Deriving logic equations for each intermediate molecule and for the final output molecule using the interactions specified in Step 2 and applying the following two rules:
    Rule 1: If a molecule has no inhibitory inputs, then the activation of at least one stimulatory input activates the molecule; and
    Rule 2: If a molecule has at least one active inhibitory input, then that molecule is inactive.
4. Constructing a digital circuit representation from the logic equations, using AND, OR, NOT and BUFFER circuit elements.

5. Identifying the feedback paths for the digital circuit representation using, e.g., the DFS algorithm (see Cormen et al., 2001), and then modeling each feedback path by, e.g., inserting a flip-flop along each feedback path.
6. Applying fault diagnosis techniques, e.g., the EPP algorithm (see the three Asadi et al. publications, 2005) to the digital circuit representation, in order to calculate the vulnerability level for each node/molecule.

Systems disclosed herein generally include a processor for executing the disclosed methods and associated memory for storage of appropriate system-related information/data. In exemplary embodiments, a user interface may also be included for use, inter alia, in inputting/selecting a target network and calculating the vulnerabilities.

Although exemplary embodiments of the present disclosure use binary logic equations, a multiple-valued logic model may just as readily be applied. For example, rather than modeling the activity of a molecule by the two states of "active" and "inactive", one can model molecule activity using a ternary logic model, e.g., "inactive," "active" and "hyperactive". Alternatively, fuzzy logic may also be used to model a molecular network. The circuit model is, therefore, generally constructed based on the logic chosen. Thus, in an exemplary embodiment of the present disclosure, an analog circuit model may be used instead of a digital circuit model when representing a target system. A dynamic system approach may also be used for modeling the network of interest, to include and analyze the variations of the network versus time. Regardless of the logic regimen employed, the systems and methods of the present disclosure are effective in establishing a circuit equivalent to a molecular network for use in, inter alia, identifying vulnerable molecules.

The systems and methods disclosed herein have a wide range of potential applications. Therefore, while exemplary embodiments generally involve analysis of human physiological systems, the systems and methods disclosed may be used to analyze any molecular network, e.g., animals, plants, bacterial molecular networks and other living or non-living systems/networks. The type of network is similarly not limited to the exemplary embodiments discussed herein. Thus, for example, genetic networks, metabolic networks, signaling networks, etc., may all be analyzed using the disclosed systems and methods.

Additional features, functions and benefits of the disclosed fault diagnosis methods will be apparent from the description of exemplary embodiments which follows, particularly when read in conjunction with the accompanying figures.

BRIEF DESCRIPTION OF THE ACCOMPANYING FIGURES

To assist those of ordinary skill in the art in making and using the disclosed systems and methods, reference is made to the accompanying figures, wherein:

FIG. 1A depicts an exemplary molecular/biological network involving seven molecules. The input molecules of the seven node toy model are A and B, the intermediate molecules are C, D, E, F, and finally G is the output molecule. The activatory and inhibitory signals are shown by connecting lines.

FIG. 1B depicts a digital circuit representation for the exemplary network of FIG. 1A. The input and output nodes (molecules) A and G are shown. The names of some molecules appear multiple times to facilitate recognition of the inputs and outputs of the logic gates. A small dot is used to show where a wire is branched out from another wire.

FIG. 1C depicts a further exemplary molecular/biological network including ligands EGF, insulin and TNF. The caspase3-FKHR network has a total of 22 nodes. The input molecules are EGF, insulin and TNF, and the output molecules are caspase3 and FKHR. The node ComplexI includes TNFR and TRADD-RIP-TRAF2, whereas the node ComplexII stands for TRADD-RIP-TRAF2 and FADD.

FIG. 1D depicts a digital electronic caspase3-FKHR circuit based on the caspase3-FKHR molecular network shown in FIG. 1C.

FIG. 1E sets forth a truth table for the exemplary network of FIGS. 1C and 1D which shows the binary logic values of the outputs, FKHR and caspase3, when different inputs are applied to the circuit. The first three columns include all possible input scenarios, whereas the last three columns are computed according to circuit logic equations and the basic properties of binary operations.

FIG. 1F is a tabular presentation of calculated vulnerabilities for molecules in the caspase3-FKHR network, with the output node FKHR and its preceding BUFFER removed. These vulnerabilities are calculated using the EPP algorithm and are sorted from high to low. In both circuits, AKT shows the highest vulnerability level.

FIG. 2A depicts a p53 molecular network involving 49 nodes (molecules). The input molecules are insulin and PDGF, and the output molecule is p53. To make the figure less crowded, small circles are used to show that a signal coming from one molecule may target several other molecules.

FIG. 2B depicts a digital circuit representation for the exemplary network of FIG. 2A derived based on the p53 molecular network shown in FIG. 2A. There are seven feedback paths in this circuit, initiated from $Ca^{2+}$, JNK, caspase3, Gab1, PLCβ, Abl and PKC. These feedbacks are identified using the DSF algorithm, and then one flip-flop (FF) is inserted in each path. For example, there is an FF at the upper right corner of the circuit, with PKC and PKC_FF as its input and output, respectively. The name PKC_FF appears again at the lower left corner of the circuit, which means that PKC is "fed back" from the right side of the circuit to the left side. The feedback wire itself is not shown, to make the circuit diagram easier to read.

FIG. 2C is a tabular presentation of calculated vulnerabilities for molecules in the disclosed p53 molecular network calculated using the EPP algorithm, and sorted from high to low.

FIG. 2D depicts a bar graph of molecular vulnerability values for the disclosed p53 system. The vulnerabilities of PIP2, AKT, caspase3 and PP2A are greater than 0.5, whereas those of caspase8, PI3K, Abl, PIP3, PTEN and PKC are between 0.1 and 0.5. The vulnerabilities of the rest of the molecules are smaller than 0.1.

FIG. 2E depicts a bar graph of vulnerability value distributions for the disclosed p53 molecular network. The number at the top of each black bar represents the total number of molecules whose vulnerabilities fall within the range specified by the location of that bar. For example, there are 38 molecules such that their vulnerabilities are between 0 and 0.1.

FIG. 3A depicts an exemplary CREB signaling pathway involving 64 nodes (molecules). The input molecules are glutamate, dopamine, GABA, serotonin, Ach, adenosine and enkephalin, and the output molecule is CREB. To make the figure less crowded, small circles are used to show that a signal coming from one molecule may target several other molecules. Also small squares are employed to illustrate that several different molecules may target one molecule.

FIG. 3B depicts a digital circuit representation for the exemplary CREB signaling pathway of FIG. 3A. There are five feedback paths in this circuit, initiated from PLCγ, PP2A, calmodulin, PKA and PKC. These feedbacks are identified using the DSF algorithm, and then one flip-flop (FF) is inserted in each path. For example, there is an FF at the upper right corner of the circuit, with PKA and PKA_FF as its input and output, respectively. The name PKA_FF appears again at the upper left corner of the circuit, which means that PKA is "fed back" from the right side of the circuit to the left side. The feedback wire itself is not shown, to make the circuit diagram easier to read.

FIG. 4A is a tabular presentation of calculated vulnerabilities for molecules in the disclosed CREB signaling pathway calculated using the EPP algorithm, and sorted from high to low.

FIG. 4B depicts a bar graph of vulnerability values for the disclosed CREB system. The vulnerabilities of calmodulin, $Ca^{2+}$, cAMP, Galphai, AC2, AC1, AC5, PKA, P/Q type CaCh and PP2A are greater than or equal to 0.5, whereas those of Gbetagamma, CaMKII, PP2B, CaMKIV, CaMKK, CREM, N-type CaCh, NMDAR, PI3K, PIP3, PDK1 and RSK are between 0.1 and 0.5. The vulnerabilities of the rest of the molecules are smaller than 0.1.

FIG. 4C depicts a bar graph of vulnerability value distributions for the disclosed CREB system. The number at the top of each black bar represents the total number of molecules whose vulnerabilities fall within the range specified by the location of that bar. For example, there are 41 molecules such that their vulnerabilities are between 0 and 0.1.

DESCRIPTION OF EXEMPLARY EMBODIMENT(S)

Figure 1A:
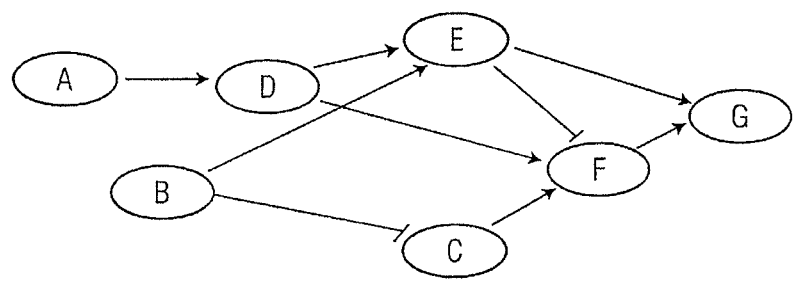

Advantageous systems and methods for identifying molecular vulnerabilities in biological pathways are disclosed herein. The disclosed systems and methods generally involve modeling a biological system as a digital logic circuit and then using probability propagation algorithms to determine molecular vulnerabilities. In exemplary embodiments, the disclosed systems and methods may be used to facilitate the diagnosis, isolation and/or treatment of disease.

The currently disclosed systems and methods involve modeling a disorder at the molecular level as a faulty system, in which one or more molecules in the complex intracellular network are dysfunctional. As noted above, recent progress in genome-wide and proteome-wide expression analysis of biological systems provides a valuable picture of the "expression levels" of the molecules. According to exemplary embodiments of the present disclosure, the "functionality" of each molecule determines the overall performance of the molecular system.

It is well recognized that there are similarities between digital electronic circuits and genetic/signaling networks (see Sauro et al., 2004). In a manufacturing facility, a digital circuit is manufactured based on a particular design and is supposed to provide a specific function. However, during the fabrication process, physical defects such as faulty transistors, open and short wires, etc., may arise, which cause the manufactured circuit not to function correctly (according to the design specifications). Testing of digital circuits and systems is therefore necessary to separate defective manufactured parts from the non-defective ones, in order to guarantee the delivery of fault-free products to customers. The test itself is an assessment of the manufactured circuit, according to a set of criteria. During the lifetime operation of electronic systems, the correct functionality is a key aspect and is typically referred to as reliability. Similar analysis is applies herein to molecular networks.

In order to determine the most vulnerable molecules in a network of molecules, the disclosed systems and methods take advantage of a class of electronic circuit reliability analysis techniques known as vulnerability assessment methods. Such methods provide numerical values for the vulnerability of the operation of the entire molecular system to the dysfunction of each individual molecule. A high vulnerability for a molecule means that with high probability, the whole signaling network does not operate correctly, if that particular molecule is dysfunctional. Therefore, it is possible to conclude that such molecule plays a key role in changing the state of the system from normal to faulty (abnormal). Identification of such important molecules, i.e., with high vulnerability levels, in networks of interest is a major step towards understating the molecular basis of complex human diseases. From the drug development perspective, vulnerability assessment provides a set of candidate molecules to target.

Thus, in order to calculate the molecular vulnerability for a biological network, a mathematical model of the network system is created. In general, many different types of models may be used to represent a molecular network, e.g., differential equations, algebraic, Boolean, Bayesian, graphical, etc. (See also, Klipp et al., 2005; Husmeier et al., 2005; Bajic and Wee, 2005; Papin et al., 2005; Sauro and Kholodenko, 2004; Saez-Rodriguez et al., 2004; Ideker and Lauffenburger, 2003; Bower and Bolouri, 2001, each of which is incorporated herein by reference.) In exemplary embodiments of the disclosure, the target system is modeled using Boolean representations, wherein the state of each molecule is either active (equal to 1) or inactive (equal to 0). (Klipp et al., 2005) Indeed, analogous to digital electronic circuits, the state of a molecule may be characterized as either 1 or 0, respectively. A system model produced using Boolean representations is easily converted to a digital logic circuit. According to the present disclosure, Boolean models may advantageously be analyzed using digital electronic fault diagnosis engineering methods (Bushnell and Agarwal, 2000), in order to determine the molecular vulnerability for each molecule within a system.

Conceptually, each molecule in a network is supposed to have the ability to change between active and inactive states depending on its inhibitory and/or stimulatory inputs. Thus, in exemplary embodiments, a molecule may be said to be dysfunctional if it is "stuck" in a particular state. Biologically, this may be due to mutation and/or other structural abnormalities. It is important to note that different dysfunctional molecules may have differing degrees of effect on the overall molecular system. Thus, in exemplary embodiments, fault diagnosis techniques are used to determine those molecules which present the greatest molecular vulnerabilities for the target system. In other words, the present disclosure generally facilitates identification of those molecules that, if dysfunctional, will have the greatest adverse impact on a network. Identification of these molecules is ultimately crucial to the diagnosis and treatment of disease, e.g., arising from the malfunction of the molecular network.

In exemplary embodiments, the vulnerability of each molecule/node may be quantified as the probability of the entire system breaking down, e.g., failing to produce the correct final output, if that particular molecule/node is dysfunctional. The input(s) for each molecule are generally assumed to be statistically independent, wherein each input has the same probability (0.50) of being active (equal to 1) or inactive (equal to 0). Of course correlated and non-equiprobable inputs can be easily analyzed as well. In general, an error probability propagation method is applied in order to calculate the molecular vulnerability value for each molecule in a network. One exemplary error probability propagation method (the EPP method) which may be applied is presented by Asadi et al. (Asadi, H., Tahoori, M. B. (2005), "An Accurate SER Estimation Method Based on Propagation Probability," IEEE Design and Test Automation in Europe, 306-307; Asadi, H., Tahoori, M. B. (2005), "An analytical approach for soft error rate estimation in digital circuits," IEEE International Conference on Circuits and Systems, 2991-2994; and Asadi, H., Tahoori, M. B. (2005), "Soft error modeling and protection for sequential elements," IEEE International Symposium on Defect and Fault Tolerance of VLSI, 463-474, each of which is incorporated herein by reference). A brief overview of an exemplary EPP method is presented below. Note that the exemplary EPP method outlined herein is not limiting and that other methods and/or fault diagnosis techniques and vulnerability assessment and reliability analysis methods, e. g., Bushnell, M. L. and Agarwal, V. D. (2000) and many other books and articles, may be applied instead or in conjunction therewith, without departing from the spirit or scope of the present disclosure.

With initial reference to FIG. 1A, an exemplary molecular network involving seven molecules is depicted. For the hypothetical system depicted, molecules A and B are the input nodes and molecule G is the output node. Activation and inhibition interactions between different molecules are shown by arrows and broken lines, respectively. For example, molecule A is depicted to stimulate molecule D, whereas molecule B is depicted to inhibit molecule C. In order to mathematically represent the system, the state of each molecule may be represented by a binary value assigned to that molecule. For example, A=0 indicates that molecule A is inactive, whereas A=1 means that molecule A is active.

To assess the vulnerability of the molecular network, it is necessary to derive binary logic equations for each molecule in the network. Based on common/known physiological mechanisms for regulating signaling activity, two general rules may be applied in order to derive the logic equations for a molecular network:

Rule 1: If a molecule has no inhibitory inputs, then the activation of at least one stimulatory input activates the molecule.

Rule 2: If a molecule has at least one active inhibitory input, then that molecule is inactive (accordingly, a molecule may be active only if all its inhibitory inputs are inactive).

These general rules may be mathematically represented by applying the logical operations, OR, AND and NOT as provided herein. For example, Rule 1 may be represented using the OR operation (of activatory inputs), wherein any one stimulatory input will activate the molecule. Conversely, Rule 2 translates to the AND operation (of inverted inhibitory inputs). When a molecule has both types of activatory and inhibitory inputs, the two rules may be combined in situations wherein activity of a molecule depends on both stimulatory and inhibitory inputs, i.e., the AND of inverted inhibitory inputs is combined with the OR of activatory inputs. Using the above two rules, the following logic equations are derived for the network depicted in FIG. 1A:

$$C=B',$$

$$D=A,$$

$$E=B+D,$$

$$F=E'\times(C+D),$$

$$G=E+F.$$

In these equations, the operations ', + and × stand for the binary logic operations NOT, OR and AND, respectively. For convenience, the mathematical implications for these binary operations are outlined herein:

For the NOT operation: $0'=1$, $1'=0$;

For the OR operation: $0+0=0$, $0+1=1$, $1+0=1$, $1+1=1$; and

For the AND operation: $0\times0=0$, $0\times1=0$, $1\times0=0$, $1\times1=1$.

Next, with further reference to FIG. 1A, the process by which the above logic equations are derived is addressed. To derive the first equation, C=B', it is noted that molecule C includes only an inhibitory input from molecule B. Therefore, molecule C equals 0 (is inactive) if molecule B equals 1 (is active) and vice versa. Based on the previously provided definition for the NOT operation, molecule C is therefore equal to the NOT of molecule B, e.g., C=B'.

The second equation D=A is similarly derived by noting that molecule D receives only an activatory input from molecule A. Thus, if molecule A is equal to 0 (inactive), then molecule D is equal to 0 (inactive). Moreover, if molecule A is equal to 1 (active), then molecule D will also be equal to 1 (active). Accordingly, the value for molecule D is always equal to the value for molecule A.

The third equation E=B+D is derived by applying Rule 1. Molecule E has no inhibitory inputs and is therefore activated if molecule B is active "or" molecule D is active. Thus, molecule E equal 1 (is active) if molecule B equals 1 (is active) "or" if molecule D equals 1 (is active). Hence, molecule E is the OR of molecule B and molecule D, i.e., E=B+D. The fifth equation—which solves for molecule G—is derived applying the same principle.

Based on FIG. 1A and Rule 2, the fourth and final logic equation which solves for molecule F may be derived based on the fact that, if molecule E is active, then molecule F is inactive (molecule E is an inhibitory input for molecule F). Furthermore, when molecule E is inactive, then molecule F will depend on the other inputs. In this example, there are two activatory inputs, which result in the combined input of C+D. Overall, it is apparent that molecule F is the AND of E' and C+D, i.e., F=E'×(C+D).

Figure 1B:
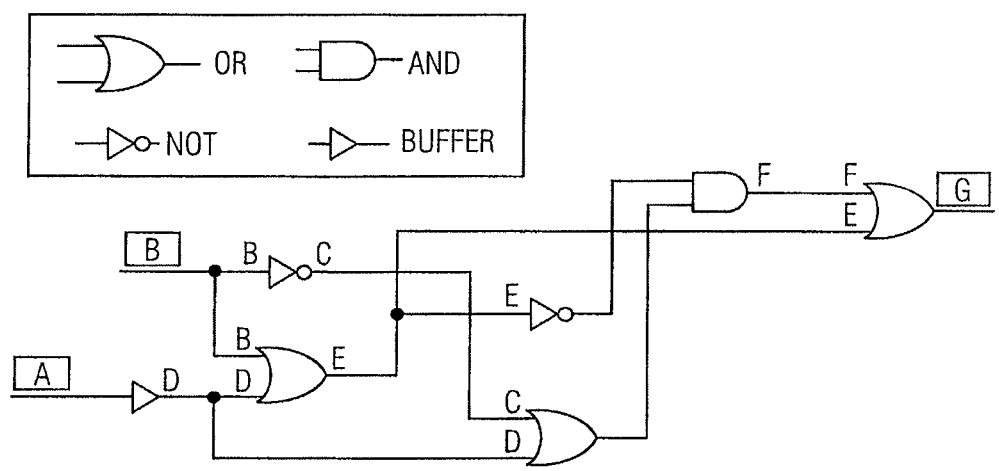

Based on the logic equations for a given system, a digital electronic circuit for that molecular network may be derived, e.g., using AND, OR, BUFFER and NOT gates (logic circuit elements). Other logic circuit elements such as XOR, etc. may be used. The digital circuit representation for the system of FIG. 1A is depicted in FIG. 1B. In the circuit depicted, a triangle with a bubble on the right vertex represents the NOT operation (an inhibitory input) and a triangle with no bubble represents a BUFFER operation (a stimulatory input). It is noted that the input and output values are the same for a BUFFER operation, e.g., if the input equals 1 (is active), then the output equals 1 (is active) and vice versa.

Once the digital circuit model for the target biological system is derived, flip-flops or other models/components may be included for each identified feedback path and molecular vulnerabilities for that system may be identified using fault diagnosis techniques. In exemplary embodiments, feedback paths in a circuit representation are identified using the depth-first search (DFS) algorithm (see Carmen et al., 2001). Other methods may be used as well. Feedback paths are modeled by a unit delay, and all the molecules/nodes are updated in a synchronous manner. Other approaches may be used to model the feedback paths. In exemplary embodiments, flip-flops are one-bit digital logic memory units inserted along identified feedback paths. An asynchronous model for the target network may include information on the delays of feedback loops, as well as other pieces of information. If such a model is available, one may need to use another vulnerability assessment method, but the principles developed herein remain the same.

Figure 1C:
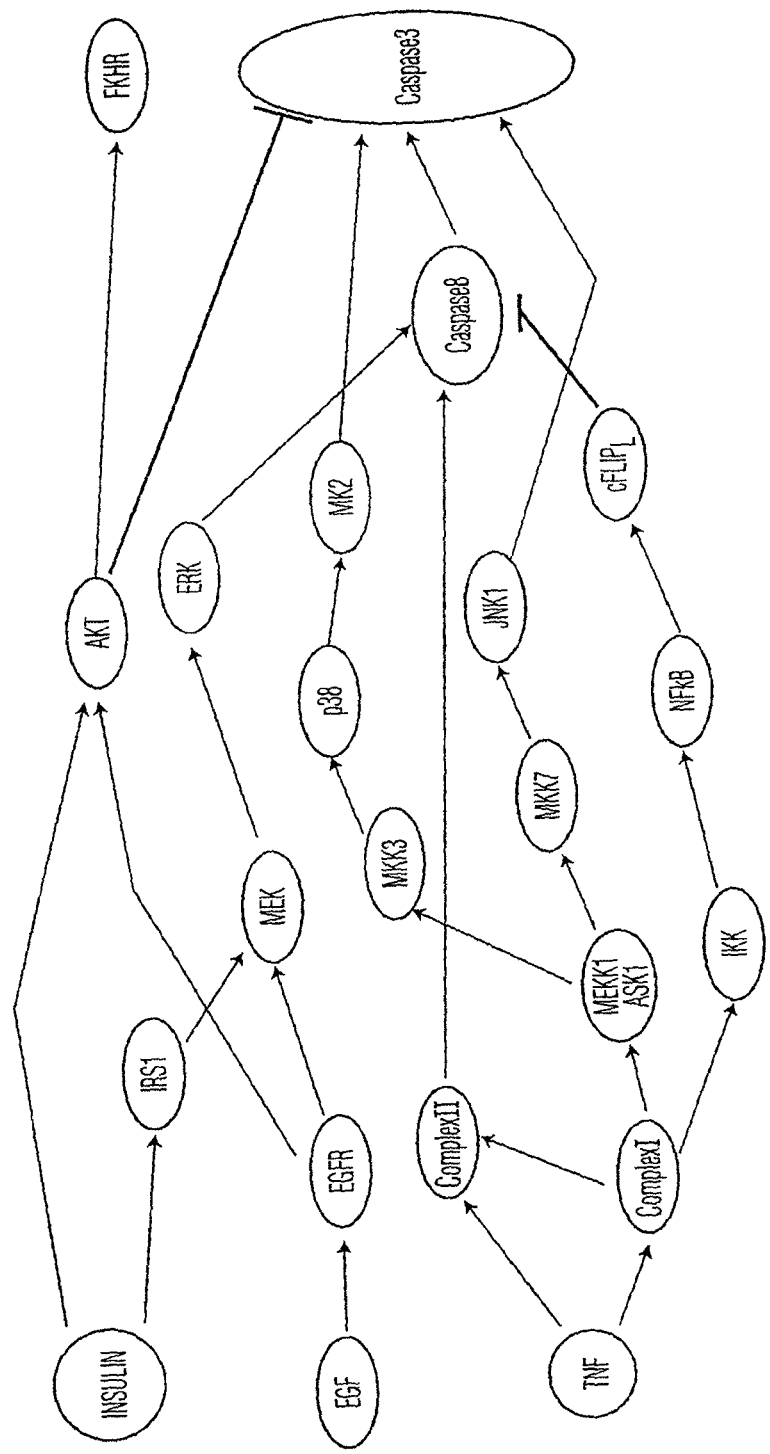

To further illustrate the disclosed systems and methods, application thereof to a small well-characterized network is provided with reference to the network of FIG. 1C. In the molecular system of FIG. 1C, the interactions between all the molecules are extensively characterized and experimentally verified (K. A. Janes et al. (2006), K. A. Janes et al. (2003). Indeed, Janes et al (2006) have studied the individual and joint effects of the three input nodes, i.e., the ligands EGF, insulin and TNF, on the activity of the two output nodes caspase3 and FKHR. Their study also shows how the activity of several intracellular intermediate molecules is modulated, in order to regulate the activity of the output nodes. The caspase3-FKHR network in this study has a total of 22 nodes, with 27 interactions among them.

Figure 1D:
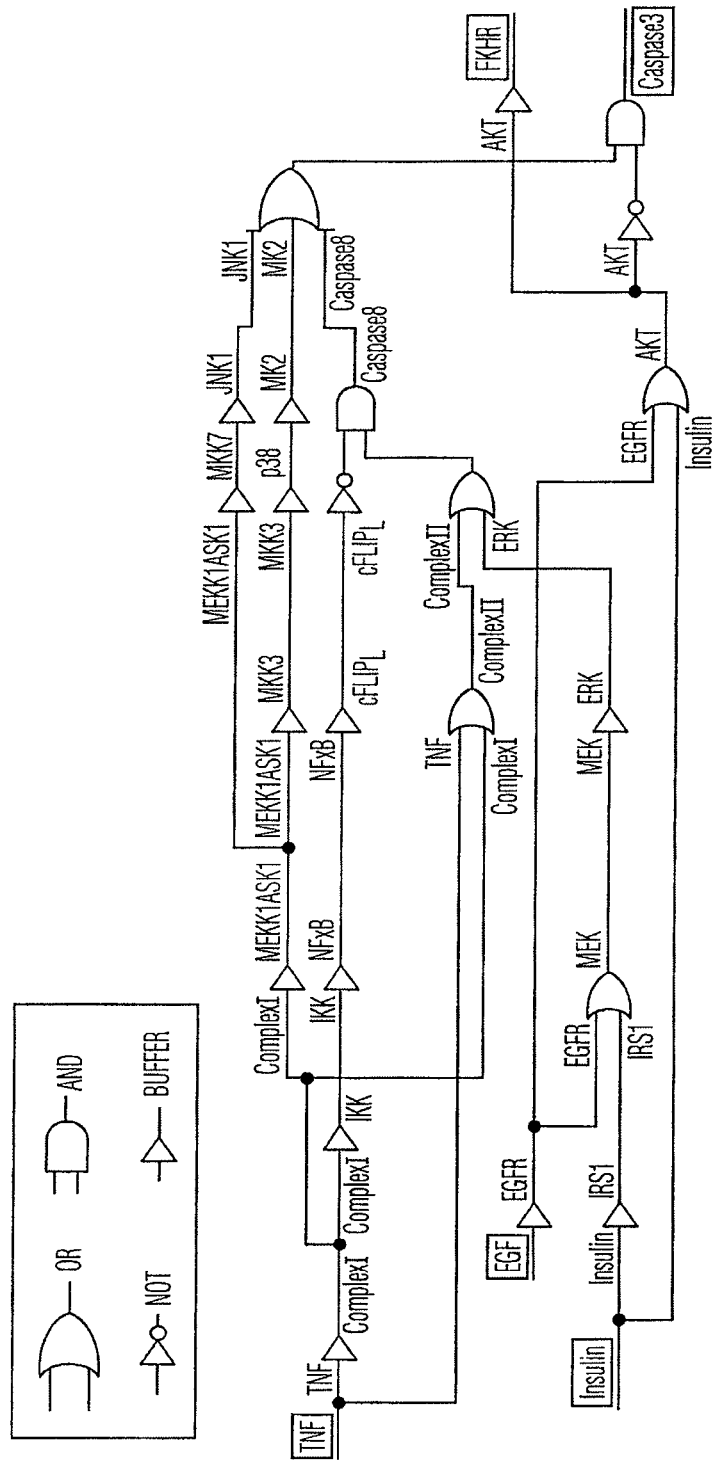

The same two rules used to derive the previous five logic equations for FIG. 1A may be applied to the caspase3-FKHR pathway (FIG. 1C), to advantageously derive a single logic equation for each node in the pathway (Table 1). The logic equation for each molecule includes all the regulatory inputs to that particular molecule, and symbolically shows how the activity of the molecule is regulated by its different inputs. More particularly, Table 1 sets forth logic equations of the caspase3-FKHR pathway of FIG. 1C wherein each logic equation specifies the input signals to a molecule using the logic operations ', + and ×, which represent NOT, OR and AND, respectively. These equations are used to generate the digital electronic caspase3-FKHR circuit (FIG. 1D) according to the present disclosure. It is noted that the symbol "'" stands for the NOT operation, the symbol "+" stands for the AND operation, and the symbol "×" stands for the OR operation.

TABLE 1

Logic equations of the Caspase3-FKHR pathway

| Molecule | Logic equation |
|---|---|
| AKT | AKT = EGFR + Insulin |
| Caspase3 | Caspase3 = AKT' × (Caspase8 + JNK1 + MK2) |
| Caspase8 | Caspase8 = cFLIP$_L$' × (ComplexII + ERK) |
| cFLIP$_L$ | cFLIP$_L$ = NFκB |
| ComplexI | ComplexI = TNF |
| ComplexII | ComplexII = TNF + ComplexI |
| EGFR | EGFR = EGF |
| ERK | ERK = MEK |
| FKHR | FKHR = AKT |
| IKK | IKK = ComplexI |
| IRS1 | IRS1 = Insulin |
| JNK1 | JNK1 = MKK7 |
| MEK | MEK = EGFR + IRS1 |
| MEKK1ASK1 | MEKK1ASK1 = ComplexI |
| MK2 | MK2 = p38 |
| MKK3 | MKK3 = MEKK1ASK1 |
| MKK7 | MKK7 = MEKK1ASK1 |
| NFκB | NFκB = IKK |
| p38 | p38 = MKK3 |

According to the logic equations derived for the caspase3-FKHR pathway, the caspase3-FKHR digital circuit may be generated (FIG. 1D) using AND, OR, BUFFER and NOT gates (four basic logic circuit elements). The truth table (FIG. 1E) of this circuit (FIG. 1D) shows the binary logic values of the outputs, FKHR and caspase3, when different inputs are applied to the circuit. The first three columns of FIG. 1E include all possible input scenarios, whereas the last three columns are calculated according to the circuit logic equations (Table 1) and the basic properties of binary operations explained previously.

Consistent with the experimental findings of Janes et al., (2006, 2003), the systems and methods of the present disclosure indicate that as long as EGF or insulin are active, caspase3 will stay inactive and therefore apoptosis will not occur. However, when both EGF and insulin are inactive and TNF is active, then caspase3 can be activated and cause apoptosis. The consistency of the experimental data provided by Jonas et al. demonstrates that the systems/methods of the present disclosure, i.e., a Boolean on/off model, have a coarse predictive power that can be verified experimentally.

To carry out the vulnerability assessment for the caspase3-FKHR circuit, the fault model of interest must be specified. There are a number of different fault models that may be used for the analysis of digital circuits. In an exemplary implementation of the present disclosure, the stuck-at-0 and stuck-at-1 fault models are employed because such fault models appear to be more biologically relevant. From the biology perspective, each molecule is supposed to change its active or inactive state, according to its input signals. However, if the molecule is "stuck" at a particular state, due to mutations or other structural/functional abnormalities, it can not respond properly to the input signals. The state of such a dysfunctional molecule will not change, even though it may receive stimulatory or inhibitory commands from its surrounding molecules. A node with the stuck-at-0 fault means that the logic value of that node (molecule) is always 0 (inactive), irrespective of its inputs. Similarly, a node with the stuck-at-1 fault implies that the node (molecule) is always 1 (active), and its state does not change if the inputs change. Note that other fault models may be used, e.g., to model dysfunctional molecules.

By way of example, if AKT in FIG. 1C is stuck at 1, then according to the logic equation for caspase3, i.e., Caspase3=AKT'×(Caspase8+JNK1+MK2) (Table 1), when AKT is always 1, caspase3 remains at a 0 value. This is because 1'=0 and 0×(Caspase8+JNK1+MK2)=0, as listed in the last column of FIG. 1E. By comparing the last two columns of FIG. 1E, the activity of caspase3 with "normal AKT" and "stuck-at-1 AKT", it is apparent that the only chance of caspase3 activation and the subsequent apoptosis under normal conditions is taken away because of the faulty AKT. This change in the state of caspase3 is shown in FIG. 1E and is supported by the experimental findings of many groups of cancer biologists that the hyperactivity of AKT (i.e., stuck-at-1) is associated with malignant transformation (J. Luo et al. (2003)). The binary logic model disclosed herein supports the long standing hypothesis of cancer that oncogenes may block adaptive cellular apoptosis by hyperactivating AKT. On the other hand, hyperactivity of AKT (stuck at 1) is a selected mechanism by cancerous cells to overcome the apoptotic stimuli (forcing the state of caspases3 from 1 to 0), which can result in the subsequent uninhibited cell division and cancer.

After choosing the biologically-relevant stuck-at fault model, the disclosed systems/methods may be used to define the vulnerability of a node (molecule). By definition, the vulnerability value of a node is the probability that the system fails (incorrect system output), if that particular node is faulty (dysfunctional). To determine the vulnerability of the network to the dysfunction of each individual molecule, the input signals may be considered to be statistically independent, such that each input molecule takes 0 and 1 with the same probability of 0.5. One can also assume correlated and non-equiprobable inputs. By applying the error probability propagation (EPP) method (H. Asadi, M. B. Tahoori (2005)) to the caspase3-FKHR circuit (FIG. 1D), derived from the logic equations of this pathway (Table 1), the vulnerability values of all the molecules in the caspase3-FKHR network may be advantageously calculated (FIG. 1F).

The molecules of FIG. 1F are sorted based on their vulnerability levels. As expected, the vulnerabilities of the output nodes are always 1, since if the output nodes are dysfunctional, the pathway will not function correctly. Based on FIG. 1F, the caspase3-FKHR pathway shows the highest vulnerability to the dysfunction of AKT. Such a high vulnerability for AKT, compared to the other components, might be attributed to the fact that AKT is the immediate upstream regulator of both the output nodes (FIG. 1C). To clarify this issue, the output node FKHR may be removed from the pathway of FIG. 1C. This gives a three-input one-output network, with caspase3 as the output node. Using the same vulnerability assessment algorithm, the vulnerabilities of all the nodes were re-calculated (FIG. 1F). Interestingly, still the vulnerability of AKT is higher than the other molecules and components. This result implies the critical role of AKT in this network. Such a high vulnerability for AKT is further considered below in connection with the exemplary analysis of the p53 network.

In both caspase3 and p53 networks, the vulnerability of AKT is almost 0.87. As a biological interpretation for this result in the disclosed three-input one-output caspase3 network, it is noted that the vulnerability of 0.87 for AKT means that if it is dysfunctional, then on average, for 87% of all possible ligand binding incidents (input signals), the cell will not be able to correctly regulate the activity of caspase3 (the output node). It is noteworthy that the computed vulnerabilities (FIG. 1F) are insensitive to the presence or absence of some nodes which have minor effects on the vulnerabilities of the rest of the nodes in the pathway. For example, it is possible to remove p38 from FIG. 1C and allow MKK3 to activate MK2 directly. This modification did not change the vulnerabilities listed in FIG. 1F. In addition, removal of NFκB node also did not change the vulnerability values listed in FIG. 1F. Removal of both p38 and NFκB also did not result in an observed change in the vulnerabilities.

Figure 2A:
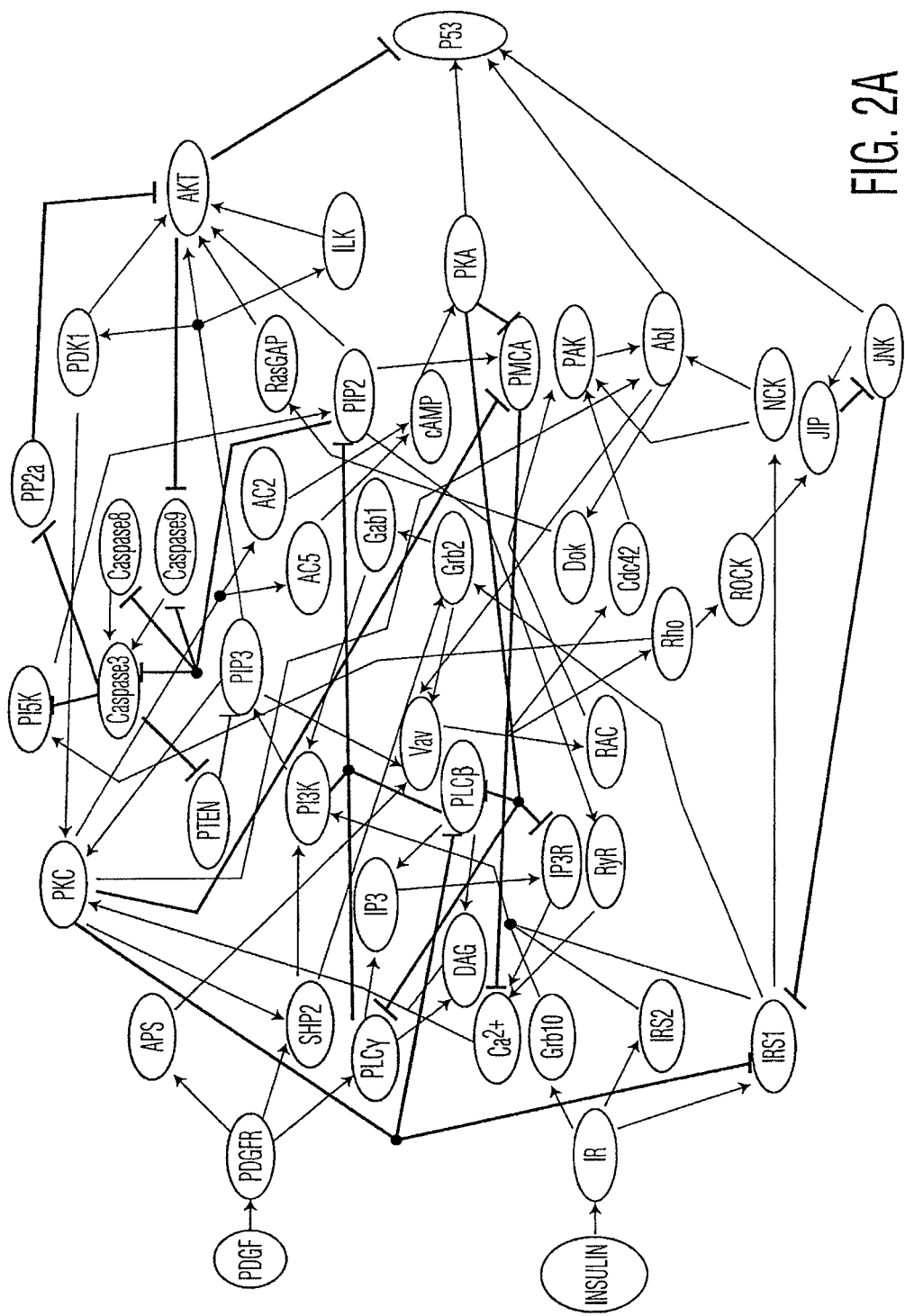

A further exemplary application of fault diagnosis techniques is herein discussed as applied to a further molecular network, the p53 system, with numerous inter-molecular interactions within the network (FIG. 2A). Unlike the caspase3-FKHR pathway (FIG. 1C) where the entire network is built up experimentally, the p53 network is constructed according to the pairs of experimentally-verified molecular interactions reported in the literature, following the same approach as Ma'ayan et al. (2005). Input nodes are the two ligands insulin and PDGF, and the output node is the transcription factor p53. The p53 tumor suppressor is a transcriptional activator of several genes that ultimately causes cell cycle arrest, cellular senescence or apoptosis. p53 has been found mutated or functionally inactivated in more than half of all human cancers. Specific interactions among molecules of this network are derived using available software and databases, e.g., UCSD-Nature Signaling Gateway (http://www.signaling-gateway.org/), SAVI (http://www.mssm.edu/labs/iyengar/resources/software/SAVI/), and Science/STKE Database of Cell Signaling (http://stke.sciencemag.org/cm/).

The validity of each individual interaction in this network (FIG. 2A) may be verified from the published literature in order to include the most reliable interactions. The resulting network, called the p53 pathway, has a total of 49 molecules, with 94 inter-molecular interactions which are summarized in Listing 1.

Listing 1

Inter-Molecular Interactions of the p53 Pathway

Abl to Dok, Abl to p53, Abl to Vav, AC2 to cAMP, AC5 to cAMP, AKT to CASPASE9, AKT to p53, APS to Vav, $Ca^{2+}$ to AC5, $Ca^{2+}$ to PKC, cAMP to PKA, CASPASE3 to PIP5K, CASPASE3 to PP2A, CASPASE3 to PTEN, CASPASE8 to CASPASE3, CASPASE9 to CASPASE3, Cdc42 to PAK, DAG to PKC, Dok to RasGAP, Gab1 to PI3K, Grb10 to PI3K, Grb2 to Gab1, Grb2 to Vav, ILK to AKT, Insulin to IR, IP3 to IP3R, IP3R to $Ca^{2+}$, IR to Grb10, IR to IRS1, IR to IRS2, IRS1 to Grb2, IRS1 to NCK, IRS1 to PI3K, IRS2 to PI3K, JIP to JNK, JNK to IRS1, JNK to JIP, JNK to p53, NCK to Abl, NCK to PAK, PAK to Abl, PDGF to PDGFR, PDGFR to APS, PDGFR to PLCγ, PDGFR to SHP2, PDK1 to AKT, PDK1 to PKC, PI3K to PIP3, PIP2 to AKT, PIP2 to CASPASE3, PIP2 to CASPASE8, PIP2 to CASPASE9, PIP2 to PMCA, PIP2 to RyR, PIP3 to AKT, PIP3 to ILK, PIP3 to PDK1, PIP3 to PKC, PIP3 to Vav, PIP3K to PIP2, PIP5K to PIP2, PKA to IP3R, PKA to p53, PKA to PLCβ, PKA to PLCγ, PKA to PMCA, PKC to Abl, PKC to AC2, PKC to AC5, PKC to IRS1, PKC to PLCβ, PKC to PMCA, PKC to SHP2, PLCβ to DAG, PLCβ to IP3, PLCβ to PIP2, PLCγ to DAG, PLCγ to IP3, PLCγ to PIP2, PMCA to $Ca^{2+}$, PP2A to AKT, PTEN to PIP3, Rac to PAK, RasGAP to AKT, Rho to PIP5K, Rho to ROCK, Rock to JIP, RyR to $Ca^{2+}$, SHP2 to Gab1, SHP2 to Grb2, SHP2 to PI3K, Vav to Cdc42, Vav to Rac, Vav to Rho The same two rules used to derive the previous five logic equations for the molecular network of FIG. 1A were applied to the p53 pathway (FIG. 2A) to derive a single specific logic equation for every individual molecule in the p53 pathway (Table 2).

TABLE 2

Logic equations of the p53 pathway

| Molecule | Logic equation |
| --- | --- |
| Abl | Abl = NCK + PKC + PAK |
| AC2 | AC2 = PKC |
| AC5 | AC5 = $(Ca^{2+})' \times$ PKC |
| APS | APS = PDGFR |
| $Ca^{2+}$ | $Ca^{2+}$ = PMCA' × (IP3R + RyR) |
| cAMP | cAMP = AC2 + AC5 |
| CASPASE3 | CASPASE3 = PIP2' × (CASPASE8 + CASPASE9) |
| CASPASE8 | CASPASE8 = PIP2' |
| CASPASE9 | CASPASE9 = PIP2' × AKT' |
| Cdc42 | Cdc42 = Vav |
| DAG | DAG = PLCβ + PLCγ |
| Dok | Dok = Abl |
| Gab1 | Gab1 = SHP2' × Grb2 |
| Grb2 | Grb2 = IRS1 + SHP2 |
| Grb10 | Grb10 = IR |
| ILK | ILK = PIP3 |
| IP3 | IP3 = PLCβ + PLCγ |
| IP3R | IP3R = PKA' × IP3 |
| IR | IR = Insulin |
| IRS1 | IRS1 = JNK' × PKC' × IR |
| IRS2 | IRS2 = IR |
| JIP | JIP = ROCK + JNK |
| JNK | JNK = JIP' |
| NCK | NCK = IRS1 |
| p53 | p53 = AKT' × (Abl + PKA + JNK) |
| PAK | PAK = Cdc42 + NCK + Rac |
| PDK1 | PDK1 = PIP3 |
| PDGFR | PDGFR = PDGF |
| PI3K | PI3K = Gab1 + Grb10 + IRS1 + IRS2 + SHP2 |
| PIP2 | PIP2 = PI3K' × PLCβ' × PLCγ' × PIP5K |
| PIP3 | PIP3 = PTEN' × PI3K |
| PIP5K | PIP5K = CASPASE3 ' × Rho |
| PKA | PKA = cAMP |
| AKT | AKT = PP2A' × (ILK + PDK1 + PIP2 + PIP3 + RasGAP) |
| PKC | PKC = PDK1 + PIP3 + DAG + $Ca^{2+}$ |
| PLCβ | PLCβ = PKA' × PKC' |
| PLCγ | PLCγ = PKA' × PDGFR |
| PMCA | PMCA = PKA' × PKC' × PIP2 |
| PP2A | PP2A = CASPASE3' |
| PTEN | PTEN = CASPASE3' |
| Rac | Rac = Vav |
| RasGAP | RasGAP = Dok |
| Rho | Rho = Vav |
| ROCK | ROCK = Rho |
| RyR | RyR = PIP2 |
| SHP2 | SHP2 = PDGFR + PKC |
| Vav | Vav = Abl + APS + Grb2 + PIP3 |

Figure 2B:
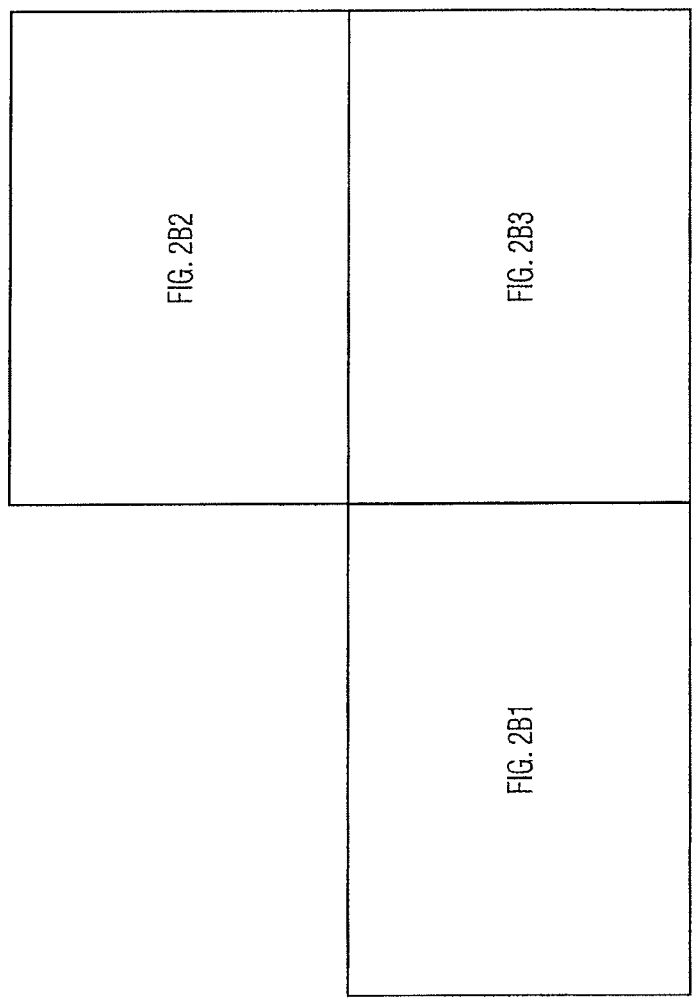

Based on the logic equations derived for the p53 pathway, the p53 digital circuit may be generated (FIG. 2B) using AND, OR, BUFFER and NOT gates (logic circuit elements). Seven combinational feedback paths in this circuit were identified using the depth-first search (DFS) algorithm (Cormen et al. (2001)). One flip-flop is then inserted in each feedback path. A flip-flop is a one-bit digital logic memory unit, shown by FF in FIG. 2B. By applying the error probability propagation (EPP) method (Asadi et al. (2005)) to the p53 circuit (FIG. 2B), which are derived from the logic equations of this pathway as summarized in Table 2, it is possible to compute the vulnerability values of all the molecules in the p53 network (FIG. 2C) according to the present disclosure.

Before discussing the results, an exemplary molecular vulnerability assessment algorithm according to the present disclosure is discussed, whereby the vulnerability of a cellular signaling network to the dysfunction of its components can be calculated.

1—Specify the inputs nodes (such as ligands, receptors, secondary messengers, etc.) and the output node (such as different transcription factors relevant to the input signal), as well as the intermediate molecules that allow the input signals to propagate from the inputs to the output. Then specify the type of the interactions among the molecules (stimulatory or inhibitory), using the existing literature. Other typos of interactions may be specified and used.

2—Use Rule #1 and Rule #2 to derive a binary logic equation for every intermediate molecule and the output molecule, using the interactions specified in Step 1. Other types of interaction rules (alone or in conjunction with Rules #1 and #2) and equations may be used.

3—Construct the digital circuit of the network from the binary logic equations of Step 2, using the AND, OR, NOT and BUFFER digital circuit elements. Other types of circuits with other types of circuit elements may be constructed.

4—Identify the feedback paths of the digital circuit of Step 3, using the DFS algorithm (Cormen (2001)). Other methods can be used as well. Then insert a flip-flop in each feedback path. Other methods/components/models may be used to model the feedback paths. If there is no feedback path, proceed directly to the next step.

5—Finally, apply the EPP algorithm (Asadi et al. (2005)), or other fault diagnosis, vulnerability assessment, reliability analysis methods, to the circuit obtained in Step 4, to calculate the vulnerability levels of all the input and intermediate nodes (the vulnerability of the output node is always 1, since if the output node is dysfunctional, the pathway will not operate efficiently anyway).

Figure 2D:
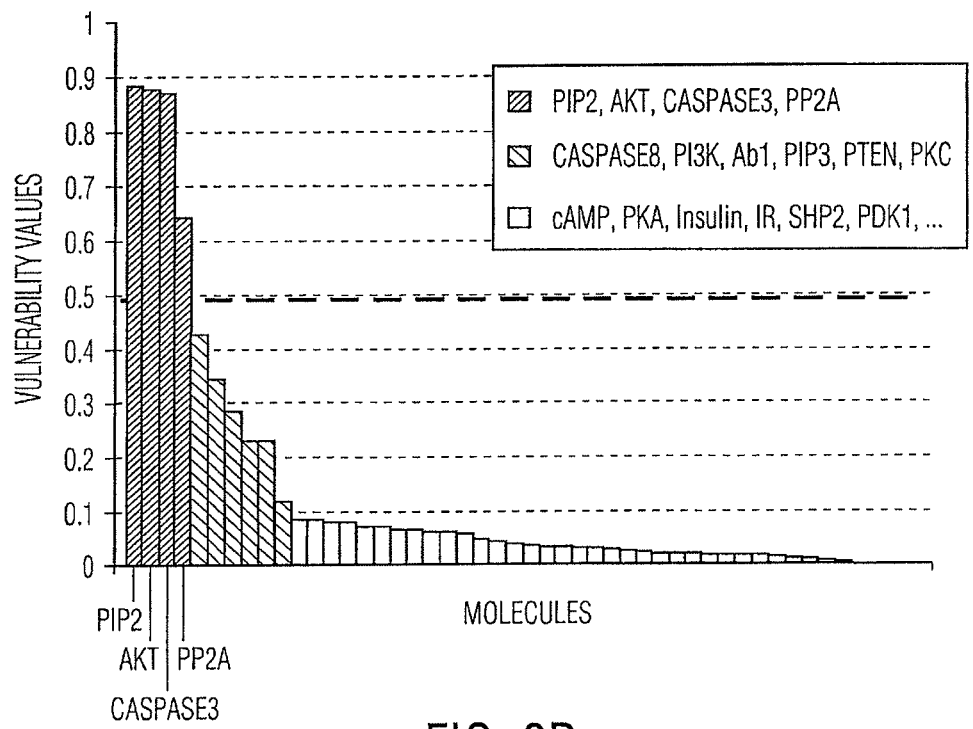
Figure 2E:
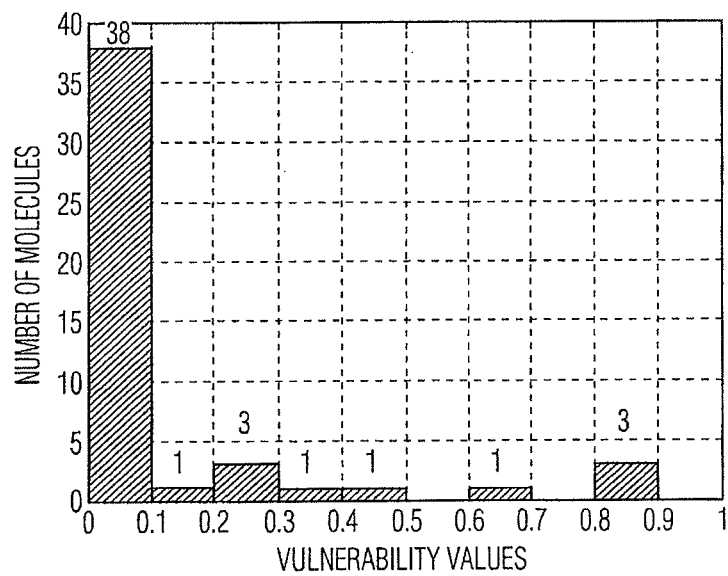

The molecules in FIG. 2C are sorted according to their vulnerability levels. As shown in FIG. 2C and FIG. 2D, the p53 pathway shows the highest vulnerability, more than 0.5, to the dysfunction of PIP2, AKT, caspases3 and PP2A. This means that if each one of these molecules is dysfunctional, from each 100 incident of ligand bindings, p53 will not function properly over 50 times. Moreover, it is demonstrated according to the present disclosure that the distribution of the vulnerability values of the molecules is highly non-uniform (FIG. 2E). For example, 38 out of the 49 molecules exhibit very low vulnerability values (less than 0.1).

The molecules to which the constructed p53 network is highly vulnerable are experimentally shown to be the key regulators of the cellular functions for which the p53 tumor suppressor gene is responsible. It is now well established that AKT plays a crucial role in regulating a number of p53 regulated functions, such as cell cycle and apoptosis (Levine et al. (2006); Brazil (2004)). From the pathology perspective, deregulation of AKT signaling pathway is known to be directly associated with some of the most prevalent and incurable human diseases such as cancer. The hyperactivity of AKT is well recognized to be a part of the pathologic process in several types of the most common human malignancies, including breast cancer, prostate cancer, lung cancer, gastrointestinal tumors, pancreatic cancer, hepatocellular carcinoma, thyroid cancer, and CNS malignancies (such as glioblastoma and gliomas). Therefore, from a pathology perspective, the most vulnerable kinase that this novel fault diagnosis approach has identified is consistent with published literature for several disease conditions. This result shows that the molecules diagnosed as faulty by the disclosed system/method are experimentally known to contribute to the system failure and cause significant pathology in humans, thereby confirming/validating the reliability of the disclosed systems and methods. Of note, the high vulnerabilities of PIP2 and PP2A are probably due to their close connections with AKT (FIG. 2A). On the other hand, the large vulnerability of caspase3 might be correlated with the findings that it plays a major role in p53 regulated apoptosis, is inhibited by PIP2, and can cause the inhibition of PP2A.

Figure 3A:
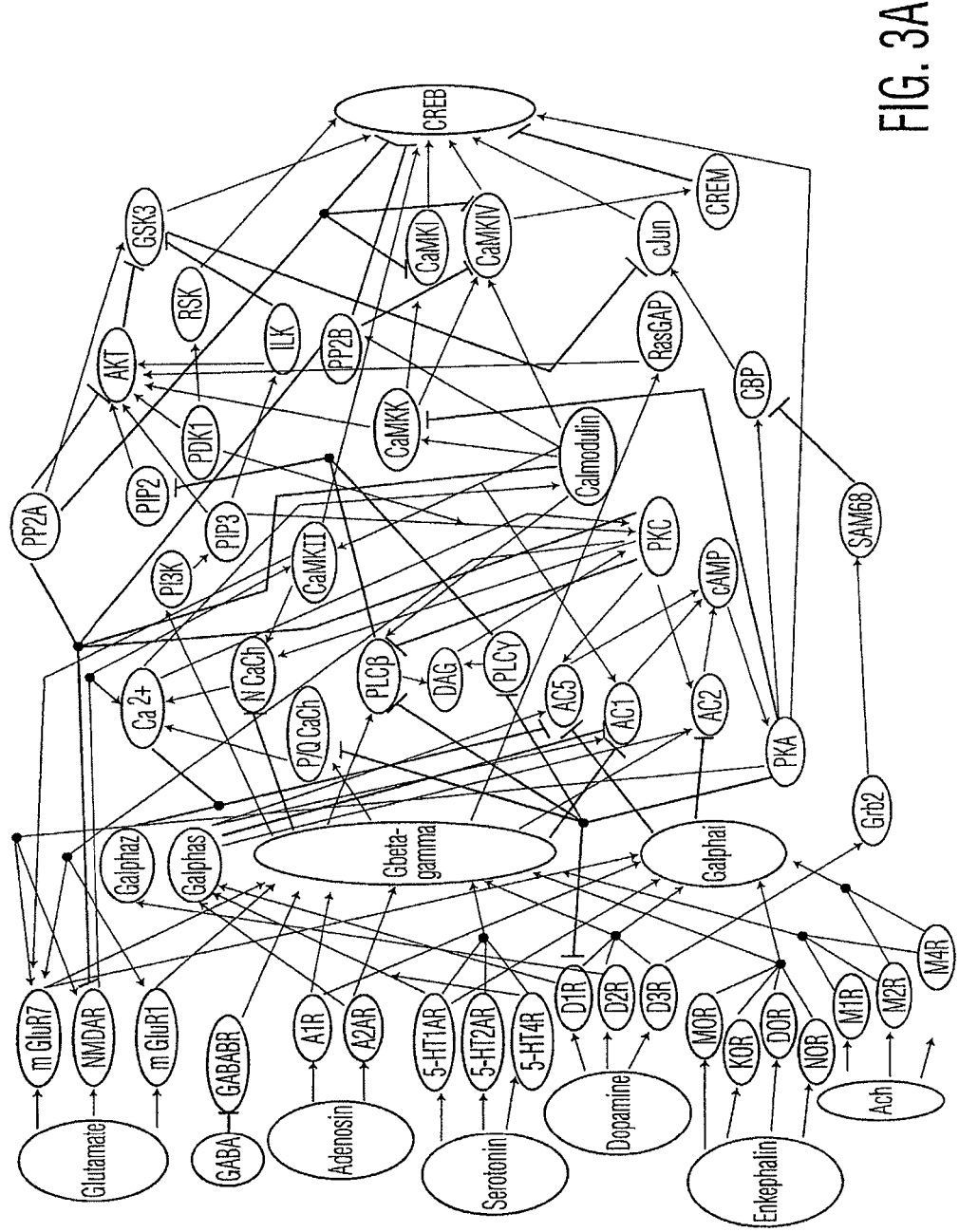

In a further exemplary embodiment of the present disclosure, a more complex neuronal network in the nervous system was constructed following the same approach as Ma'ayan et al. (2005) to construct large molecular networks. The output node is the transcription factor CREB, and the input nodes are seven major ligands in nervous system including glutamate, dopamine, GABA, serotonin, Ach, adenosine and enkephalin. The total number of interacting molecules in the CREB network (FIG. 3A) is 64, with 152 inter-molecular interactions among them, as summarized in the following listing.

Listing 2

Inter-Molecular Interactions of the CREB Pathway

5-HT1AR to Galphas, 5-HT1AR to Galphaz, 5-HT1AR to Gbetagamma, 5-HT2AR to Gbetagamma, 5-HT4R to Galphas, 5-HT4R to Gbetagamma, A1R to Galphai, A1R to Gbetagamma, A2AR to Galphas, A2AR to Galphas, A2AR to Gbetagamma, AC1 to cAMP, AC2 to cAMP, AC5 to cAMP, Ach to M1R, Ach to M2R, Ach to M4R, Adenosine to A1R, Adenosine to A2AR, AKT to GSK3, $Ca^{2+}$ to AC5, $Ca^{2+}$ to Calmodulin, $Ca^{2+}$ to PKC, Calmodulin to AC1, Calmodulin to CaMKII, Calmodulin to CaMKIV, Calmodulin to CaMKK, Calmodulin to $mGluR_7$, Calmodulin to NMDAR, Calmodulin to PLCβ, Calmodulin to PP2B, CaMKI to CREB, CaMKII to CREB, CaMKII to N-type CaCh, CaMKII to PP2A, CaMKIV to CREB, CaMKIV to CREM, CaMKK to AKT, CaMKK to CaMKI, CaMKK to CaMKIV, cAMP to PKA, CBP to cJun, cJun to CREB, CREM to CREB, D1R to Galphai, D1R to Galphas, D1R to Gbetagamma, D2R to Galphai, D2R to Galphaz, D2R to Gbetagamma, D3R to Galphai, D3R to Gbetagamma, D3R to Grb2, DAG to PKC, Dopamine to D1R, Dopamine to D2R, Dopamine to D3R, DOR to Galphai, DOR to Gbetagamma, Enkephalin to DOR, Enkephalin to KOR, Enkephalin to MOR, Enkephalin to NOR, GABA to GABABR, GABABR to Gbetagamma, Galphai to AC2, Galphai to AC5, Galphas to AC1, Galphas to AC2, Galphas to AC5, Galphaz to AC1, Galphaz to AC5, Gbetagamma to AC1, Gbetagamma to AC2, Gbetagamma to N-type CaCh, Gbetagamma to P/Q-type CaCh, Gbetagamma to PI3K, Gbetagamma to PLCβ, Gbetagamma to RasGAP, Glutamate to $mGluR_1$, Glutamate to $mGluR_7$, Glutamate to NMDAR, Grb2 to SAM68, GSK3 to cJun, GSK3 to CREB, ILK to AKT, ILK to GSK3, KOR to Gbetagamma, M1R to Gbetagamma, M2R to Galphai, M2R to Gbetagamma, M4R to Galphai, M4R to Gbetagamma, $mGluR_1$ to Gbetagamma, $mGluR_7$ to Galphai, $mGluR_7$ to Gbetagamma, MOR to Gbetagamma, NMDAR to $Ca^{2+}$, NMDAR to CaMKII, NMDAR to PLCγ, NOR to Gbetagamma, N-type CaCh to $Ca^{2+}$, P/Q-type CaCh to $Ca^{2+}$, PDK1 to AKT, PDK1 to PKC, PDK1 to RSK, PI3K to PIP2, PI3K to PIP3, PIP2 to AKT, PIP3 to AKT, PIP3 to ILK, PIP3 to PDK1, PIP3 to PKC, PKA to CaMKK, PKA to CBP, PKA to CREB, PKA to D1R, PKA to $mGluR_7$, PKA to NMDAR, PKA to P/Q-type CaCh, PKA to PLCβ, PKA to PLCγ, PKC to AC2, PKC to AC5, PKC to GSK3, PKC to $mGluR_1$, PKC to $mGluR_7$, PKC to NMDAR, PKC to N-type CaCh, PKC to PLCβ, PLCβ to DAG, PLCβ to PIP2, PLCγ to DAG, PLCγ to PIP2, PP2A to AKT, PP2A to CaMKI, PP2A to CaMKIV, PP2A to CREB, PP2A to GSK3, PP2A to NMDAR, PP2B to CaMKIV, PP2B to CREB, PP2B to NMDAR, RasGAP to AKT, RSK to CREB, SAM68 to CBP, Serotonin to 5-HT1AR, Serotonin to 5-HT2AR, Serotonin to 5-HT4R The logic equations for the CREB network (Table 3) were derived using Rule #1 and Rule #2.

TABLE 3

Logic equations of the CREB pathway

| Molecule | Logic equation |
|---|---|
| A1R | A1R = Adenosine |
| A2AR | A2AR = Adenosine |
| AC1 | AC1 = Gbetagamma' × Galphaz' × (Galphas + Calmodulin) |
| AC2 | AC2 = Galphai' × (Gbetagamma + Galphas + PKC) |
| AC5 | AC5 = Galphai' × Galphaz' × $(Ca^{2+})$' × (PKC + Galphas) |
| PP2B | PP2B = Calmodulin |
| $Ca^{2+}$ | $Ca^{2+}$ = NMDAR + N-typeCaCh + P/QtypeCaCh |
| Calmodulin | Calmodulin = $Ca^{2+}$ |
| CaMKI | CaMKI = PP2A' × CaMKK |
| CaMKII | CaMKII = Calmodulin + NMDAR |
| CaMKIV | CaMKIV = PP2A' × PP2B' × (Calmodulin + CaMKK) |
| CaMKK | CaMKK = PKA' × Calmodulin |
| cAMP | cAMP = AC1 + AC2 + AC5 |
| CBP | CBP = SAM68' × PKA |
| cJun | cJun = GSK3' × CBP |
| CREB | CREB = PP2A' × PP2B' × CREM' × (GSK3 + PKA + cJun + RSK + CaMKII + CaMKIV + CaMKI) |
| CREM | CREM = CaMKIV |
| D1R | D1R = PKA' × Dopamine |
| D2R | D2R = Dopamine |
| D3R | D3R = Dopamine |
| DAG | DAG = PLCβ + PLCγ |
| DOR | DOR = Enkephalin |
| 5-HT1AR | 5-HT1AR = Serotonin |
| 5-HT2AR | 5-HT2AR = Serotonin |
| 5-HT4R | 5-HT4R = Serotonin |
| GABABR | GABABR = GABA' |
| Galphai | Galphai = A1R + D1R + D2R + D3R + M4R + M2R + $mGluR_7$ + DOR + KOR + MOR + NOR + 5-HT1AR |
| Galphas | Galphas = A2AR + D1R + 5-HT1AR + 5-HT4R |
| Galphaz | Galphaz = D2R + 5-HT1AR |
| Gbetagamma | Gbetagamma = A1R + A2AR + M1R + M4R + M2R + D1R + D2R + D3R + GABABR + $mGluR_1$ + $mGluR_7$ + DOR + KOR + MOR + NOR + 5-HT1AR + 5-HT2AR + 5-HT4R |
| Grb2 | Grb2 = D3R |
| GSK3 | GSK3 = ILK' × AKT' × PKC' × PP2A |
| ILK | ILK = PIP3 |
| KOR | KOR = Enkephalin |
| M1R | M1R = Ach |
| M2R | M2R = Ach |
| M4R | M4R = Ach |
| $mGluR_1$ | $mGluR_1$ = PKC + Glutamate |
| $mGluR_7$ | $mGluR_7$ = Calmodulin' × (PKC + PKA + Glutamate) |
| MOR | MOR = Enkephalin |
| NMDAR | NMDAR = PKC' × PP2A' × Calmodulin' × PP2B' × (PKA + Glutamate) |
| NOR | NOR = Enkephalin |
| N-type CaCh | N-typeCaCh = Gbetagamma' × (PKC + CaMKII) |
| PDK1 | PDK1 = PIP3 |
| PI3K | PI3K = Gbetagamma |
| PIP2 | PIP2 = PI3K' × PLCβ' × PLCγ' |
| PIP3 | PIP3 = PI3K |
| PKA | PKA = cAMP |
| AKT | AKT = PP2A' × (RasGAP + ILK + PIP3 + PDK1 + PIP2 + CaMKK) |
| PKC | PKC = PDK1 + PIP3 + DAG + $Ca^{2+}$ |
| PLCβ | PLCβ = PKA' × PKC' × (Gbetagamma + Calmodulin) |
| PLCγ | PLCγ = PKA' × NMDAR |
| PP2A | PP2A = CaMKII' |
| P/Q type CaCh | P/QtypeCaCh = PKA' × Gbetagamma |
| RasGAP | RasGAP = Gbetagamma |
| RSK | RSK = PDK1 |
| SAM68 | SAM68 = Grb2 |

Figure 3B:
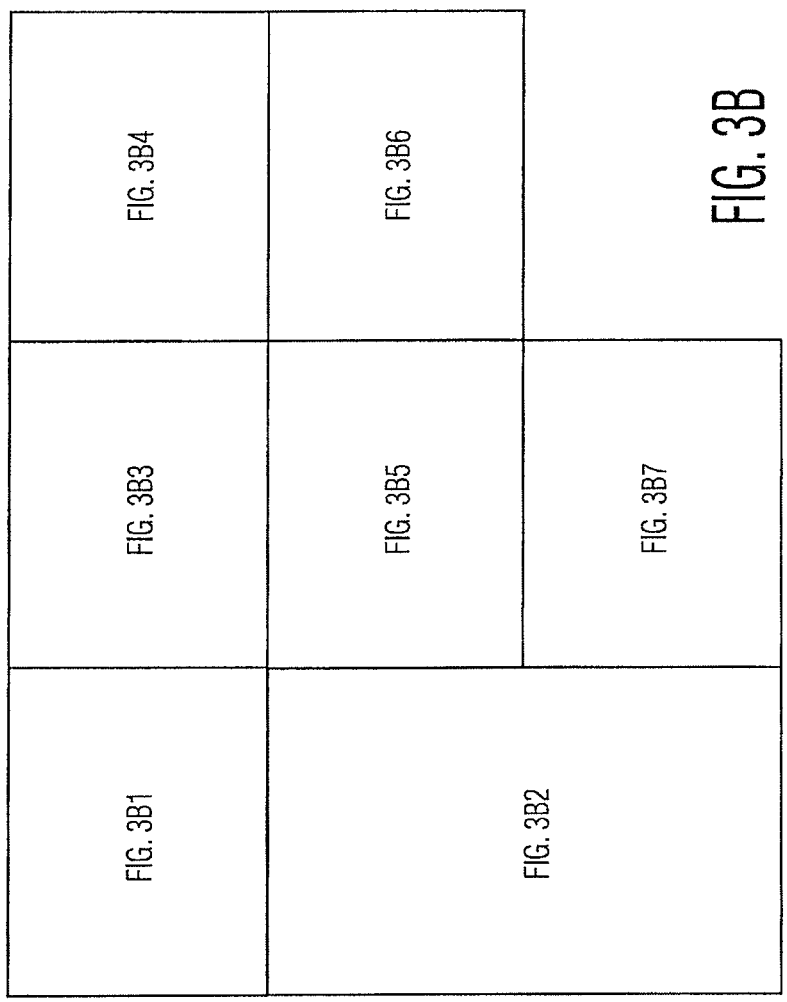

The corresponding digital electronic circuit, i.e., the CREB circuit, is shown in FIG. 3B. Using the disclosed five step vulnerability assessment algorithm set forth above, the vulnerabilities of all the molecules were calculated (FIG. 4A).

Figure 4B:
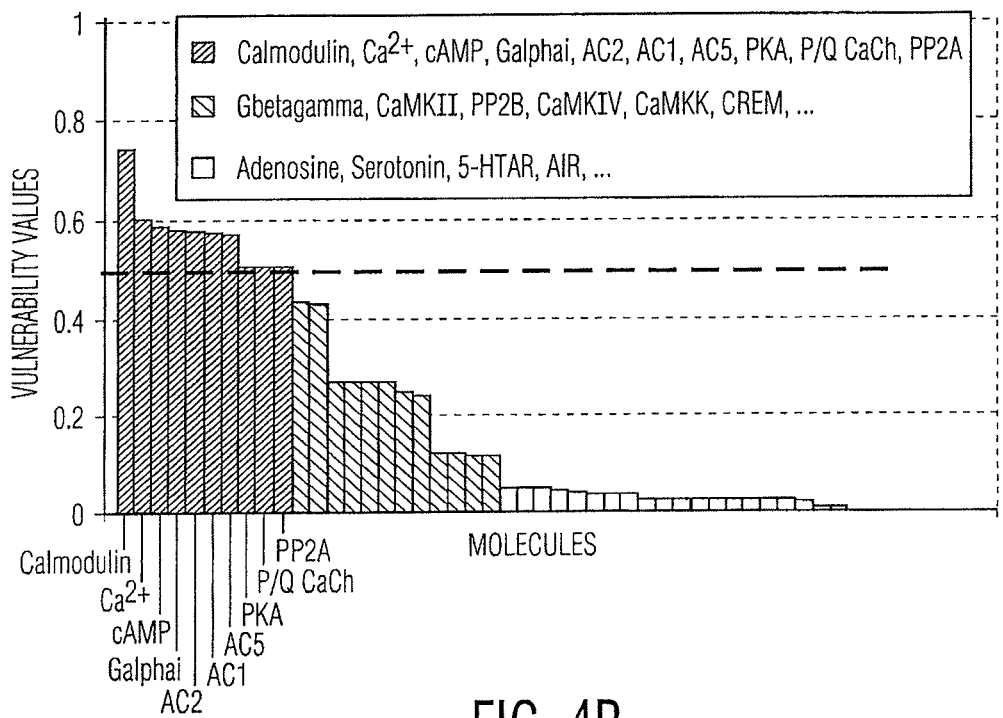
Figure 4C:
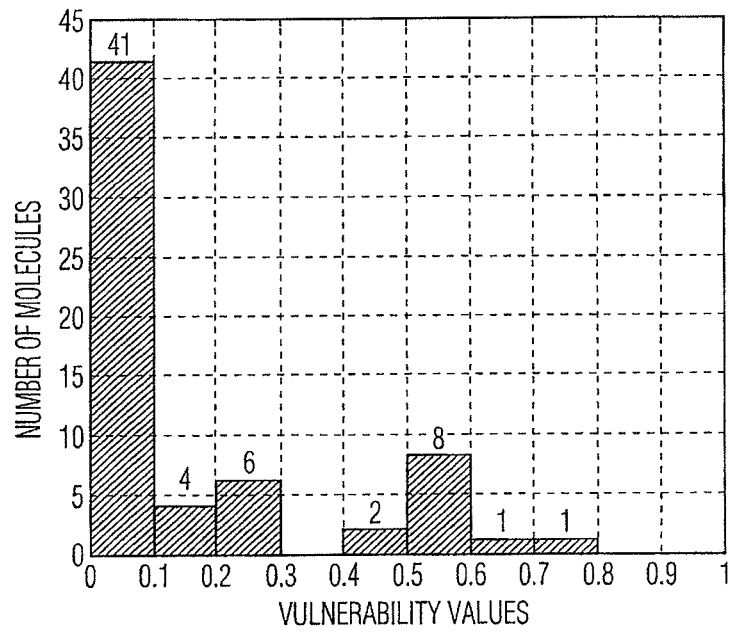

According to FIG. 4A, the molecules evidencing dysfunction that can result in the failure of the CREB function, with a probability of more than 0.5, are calmodulin, calcium, cAMP, Galphai, AC1, AC2, AC5, PKA, P/Q type calcium channel and PP2A. As shown in FIG. 4B, elements of the cAMP-dependent signaling as well as some elements of calcium signaling molecules exhibit the highest vulnerability values in the CREB circuit. Furthermore, the distribution of the vulnerability values in the CREB pathway is highly non-uniform (FIG. 4C). On the other hand, the majority of the molecules, 41 out of 64, do not contribute to the failure of CREB circuit (vulnerability values less than 0.1).

The vulnerable molecules identified in this pathway according to the disclosed systems/methods are closely related molecules, and are also physiologically relevant to the CREB function. The crucial role of the cAMP-dependent kinase in the regulation of CREB has been experimentally established for many years. A number of the most important aspects of the cognitive and executive human brain, such as learning and memory, are known to be directly regulated by cAMP-dependent CREB functions. In pathological terms, direct evidence for deregulation of PKA signaling has been reported in human disorders characterized by memory dysfunction such as Alzheimer Disease or schizophrenia. Vulnerability assessment of the CREB circuit has also identified several elements of calcium signaling to play a major role in CREB functioning. This observation is also physiologically and pathologically relevant, since the role of calcium signaling in regulation of CREB dependent functions is now well established, which is experimentally shown to have a crucial role in development of a number of pathological conditions raised from deregulation of calcium dependent signaling.

If the p53 and CREB pathways are compared, it is apparent that they share approximately 50% of their intracellular molecules. Despite this homology between the players of these two pathways, their vulnerable molecules are totally different. Furthermore, similar molecules in different networks contribute differently to the functionality of that network. This means that the cellular systems have adopted sophisticated mechanisms to achieve a desired function through a cascade of signals that employs different level of functionality for the same molecules according to that specific outcome. These mechanisms utilize the same signaling molecules in different ways to propagate the input signals to regulate the function of the output molecule.

Having described exemplary implementations of the disclosed systems and methods, additional information concerning the design, operation, implementation and functionalities are further described and/or illustrated herein below.

Vulnerability Analysis of the Logic Circuits Using the EPP Method:

The EPP method is a relatively new methodology for reliability analysis (vulnerability analysis) of logic circuits. The goal of the EPP method is to extract the error propagation probability (EPP) of all internal nodes. The EPP for a node is defined as the probability that an erroneous value for that node would propagate and result in an observable error in the system. The EPP method outlined herein advantageously exhibits improved runtime over conventional methods (several orders of magnitude faster). The presented approach uses the signal probabilities (SP) of all nodes for combinational calculations and then computes EPP values based on the topological structure of the logic circuit. The signal probability (SP) of a line l indicates the probability of l having logic value 1 (see De Vivo, M. & Maayani, S., "Characterization of the 5-hydroxytryptamine 1a receptor-mediated inhibition of forskolin-stimulated adenylate cyclase activity in guinea pig and rat hippocampal membranes." J. Pharmacol. Exp. Ther. 238, 248 (1986)). Experiments on benchmark circuits and comparison of the results with the fault injection method based on random simulation show the effectiveness and the accuracy of the presented approach (see Boronenkov, I. V. & Anderson, R. A., "The sequence of phosphatidylinositol-4-phosphate 5-kinase defines a novel family of lipid kinases." J. Biol. Chem. 270, 2881 (1995)).

Figure 5:
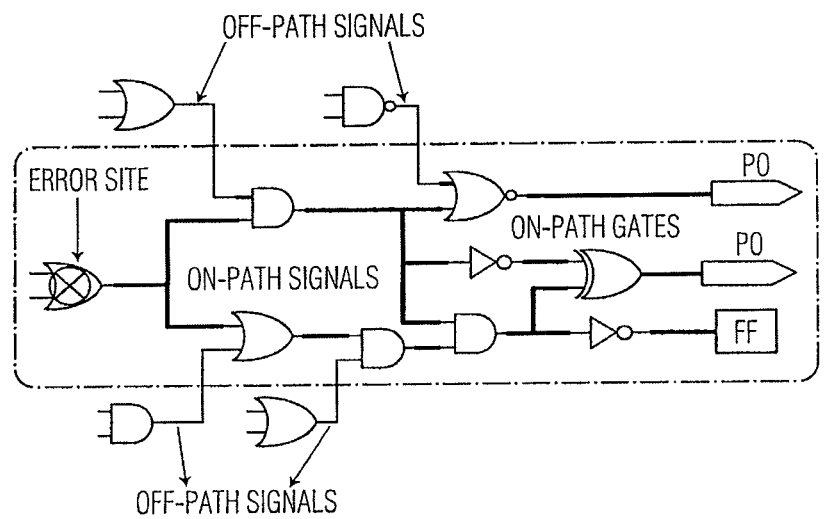
FIG. 5 depicts an exemplary path between an erroneous node to primary outputs and flip-flops for a hypothetical circuit according to the present disclosure.

In the approach outlined herein, the structural paths from the error sites to all reachable primary outputs are extracted and then traversed to compute the propagation probability of the erroneous value to the reachable primary outputs or to the reachable flip-flops. Based on the error site, nets and gates in the circuit are categorized as follows: (i) an on-path signal is a net on a path from the error site to a reachable output; (ii) an on-path gate is defined as the gate with at least one on-path input; and (iii) an off path signal is a net that is not on-path and is an input of an on-path gate. These three possibilities and associated paths are shown in FIG. 5.

Error propagation probability calculations are made for traverses paths using signal probability for off-path signals and using propagation rules for on-path signals. Various SP calculation/estimation techniques are well known in the art (see, e.g., De Waard et al., 1997, and Delcommenne et al., 1998). The problem statement can be described as follows:

Given the failure probability in node $n_i$, calculate the probability of the propagation of this error to Primary Outputs (POs) or Flip-Flops (FFs) (i.e., system failure).

Errors can be directly propagated to a primary output and cause a system failure at the same clock cycle, or they can be propagated to flip-flops repeatedly, and finally manifest as errors at a primary output several clock cycles later.

Figure 6:
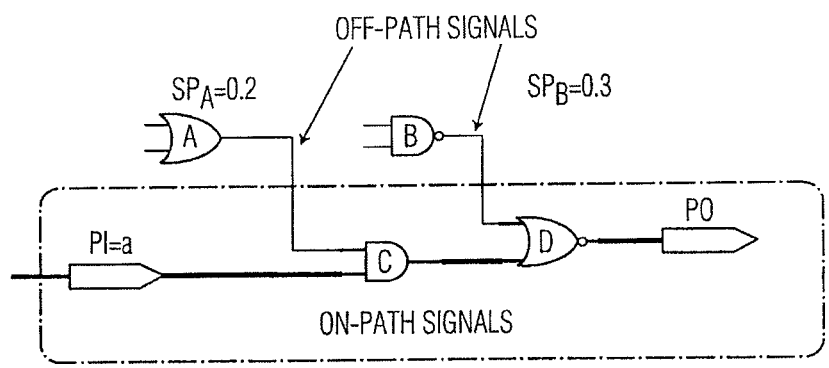
FIG. 6 depicts a simple path between an erroneous input and a primary output for a hypothetical circuit according to the present disclosure.

For illustration purposes, a simple case may be envisioned where there is only one path from the error site to an output. As this path is traversed gate by gate, the error propagation probability from an on-path input of a gate to its output depends on the type of the gate and the signal probability of other off-path signals. In the example shown in FIG. 6, the error propagation probability to the output of the gate C (AND gate) is the product of the probability of the output of gate A being 1 and the error probability at the PI ($1 \times 0.2 = 0.2$). Similarly, the EPP value at the output of the gate D (OR gate) is calculated as $0.2 \times (1 - SP_B) = 0.2 \times 0.7 = 0.14$.

In the general case in which reconvergent paths (one signal directly or indirectly drives more than one input of a logic gate) might exist, the propagation probability from the error site to the output of the reconvergent gate depends on not only the type of the gate and the signal probabilities of the off-path signals, but also the polarities of the propagated error on the on-path signals. In the presence of errors, the status of each signal can be expressed with four values:

0: no error is propagated to this signal line and the signal has an error-free value of 0.

1: no error is propagated to this signal line and it has logic value of 1.

a: the signal has an erroneous value with the same polarity as the original erroneous value at the error site (denoted by a).

$\bar{a}$: the signal has an erroneous value, but the erroneous value has an opposite polarity compared to the erroneous value at the error site (denoted by $\bar{a}$).

Based on this four-value logic, the propagation rules for each logic gate can be redefined. These probabilities, denoted by $P_a(U_i)$, $P_{\bar{a}}(U_i)$, $P_1(U_i)$, and $P_0(U_i)$, are explained as follows:

$P_a(U_i)$ and $P_{\bar{a}}(U_i)$ are defined as the probability of the output of node $U_i$ being $a$ and $\bar{a}$, respectively. In other words, $P_a(U_i)$ is the probability that the erroneous value is propagated from the error site to $U_i$ with an even number of inversions, whereas $P_{\bar{a}}(U_i)$ is the similar propagation probability with an odd number of inversions.

$P_1(U_i)$ and $P_0(U_i)$ are defined as the probability of the output of node $U_i$ being 1 and 0, respectively. In these cases, the error is blocked and not propagated.

It is noted that on-path signals, $P_a(U_i) + P_{\bar{a}}(U_i) + P_1(U_i) + P_0(U_i) = 1$, and off-path signals $P_1(U_j) + P_0(U_j) = 1$. Since the polarity of error effect propagation has been considered, the reconvergent points have already been accounted for. The error propagation calculation rules for elementary gates are shown in Table 4.

TABLE 4

Computing probability at the output of a gate in terms of its inputs.

AND
$$P_1(\text{out}) = \prod_{i=1}^{n} P_1(X_i)$$

$$P_a(\text{out}) = \prod_{i=1}^{n} [P_1(X_i) + P_a(X_i)] - P_1(\text{out})$$

$$P_{\bar{a}}(\text{out}) = \prod_{i=1}^{n} [P_1(X_i) + P_{\bar{a}}(X_i)] - P_1(\text{out})$$

$$P_0(\text{out}) = 1 - [P_1(\text{out}) + P_a(\text{out}) + P_{\bar{a}}(\text{out})]$$

OR
$$P_0(\text{out}) = \prod_{i=1}^{n} P_0(X_i)$$

$$P_a(\text{out}) = \prod_{i=1}^{n} [P_0(X_i) + P_a(X_i)] - P_0(\text{out})$$

$$P_{\bar{a}}(\text{out}) = \prod_{i=1}^{n} [P_0(X_i) + P_{\bar{a}}(X_i)] - P_0(\text{out})$$

Figure 7:
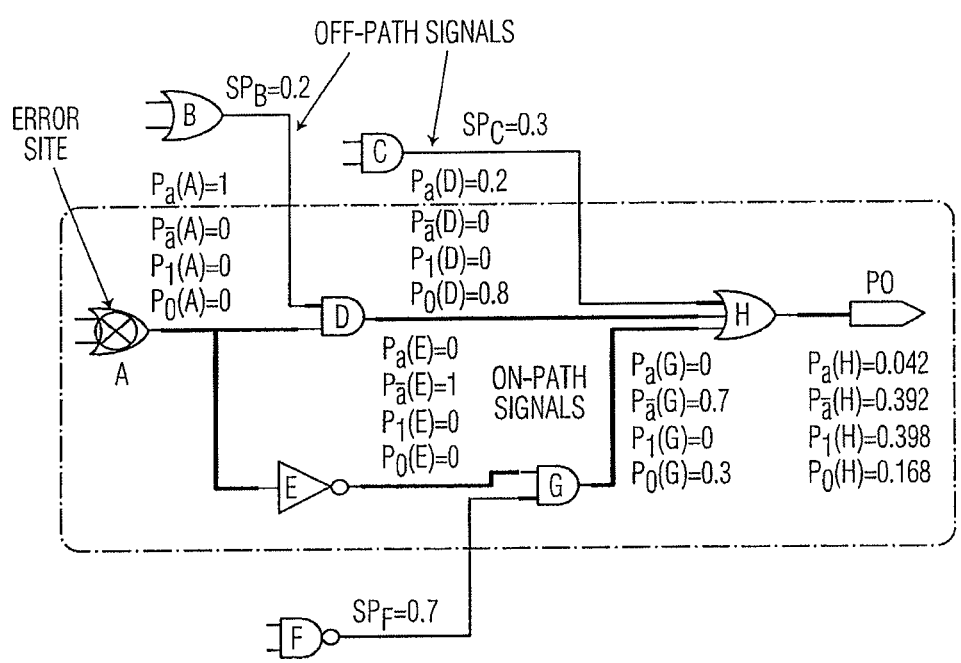
FIG. 7 depicts an example of applying error propagation rules for a reconverging path for a hypothetical circuit according to the present disclosure.

$P_1(\text{out}) = 1 - [P_0(\text{out}) + P_a(\text{out}) + P_{\bar{a}}(\text{out})]$ NOT $P_0(\text{out}) = P_1(\text{in})$, $P_1(\text{out}) = P_0(\text{in})$
$P_a(\text{out}) = P_{\bar{a}}(\text{in})$, $P_{\bar{a}}(\text{out}) = P_a(\text{in})$ To illustrate an exemplary method/technique for employing the propagation rules for reconvergent paths, reference is made to the example shown in FIG. 7. In this example, the error propagation probability from the output of gate A to PO is calculated. Here, it is assumed that gate A becomes erroneous. So, initially, $P_a(A)=1$, $P_{\bar{a}}(A)=0$, $P_1(A)=0$, and $P_0(A)=0$. These probabilities are then propagated through gates D, E, and H. As an example, the following steps may be performed according to the present disclosure to compute the error propagation probability of the erroneous value to the output of gate H.

$P_0(H) = P_0(C) \times P_0(D) \times P_0(G) = 0.7 \times 0.8 \times 0.3 = 0.168$ $P_a(H) = (P_0(C) + P_a(C)) \times (P_0(D) + P_a(D)) \times (P_0(G) + P_a(G)) - P_0(H) = (0.7) \times (0.2+0.8) \times (0.3) - 0.168 = 0.042$ $P_{\bar{a}}(H) = (P_0(C) + P_{\bar{a}}(C)) \times (P_0(D) + P_{\bar{a}}(D)) \times (P_0(G) + P_{\bar{a}}(G)) - P_0(H) = (0.7) \times (0.8) \times (0.7+0.3) - 0.168 = 0.392$ $P_1(H) = 1 - (0.168 + 0.042 + 0.392) = 0.398 \rightarrow P(H) = 0.042(a) + 0.392(\bar{a}) + 0.168(0) + 0.398(1)$ Finally, the EPP value of gate A to outputs can be computed as:

$EPP_{A\_PO} = [P_a(H) + P_{\bar{a}}(H)] = (0.042 + 0.392) = 0.434$

In general, the following exemplary algorithm shows that all paths from a given error site to all reachable outputs can be extracted and traversed and how the propagation probability rules can be applied as the paths are traversed.

The Main Algorithm

For every node, $n_i$, do:
1) Path Construction: Extract all on-path signals (and gates) from $n_i$ to every reachable primary output $PO_j$ and/or flip-flop $FF_k$. This may be achieved using forward Depth-First Search (DFS) algorithms (see Cardone et al. 1998).
2) Ordering: Prioritize signals on these paths based on their distance level using a topological sorting algorithm (see Cardone et al., 1998). Topological sort of a directed acyclic graph is an ordered list of the vertices such that, if there is an edge (u, v) in the graph, then u appears before v in the list.
3) Propagation Probabilities Computation: Traverse the paths in the topological order and apply propagation rules to compute the probability for each on-path node based on propagation probability rules (Table 5).

Using the above exemplary formulation, error propagation probabilities from an arbitrary error site to any flip-flop and/or primary output can be computed in just one pass starting from the error site to reachable output. As a result, the complexity of this approach is linear to the size of the circuit (number of logic gates). In other words, the exponential path enumeration problem is not observed in the disclosed algorithm. After computing the EPP of each node to all outputs, the overall EPP of an arbitrary node A to all primary outputs at the first clock cycle can be computed as:

$$EPP_{c=1}(A) = 1 - \prod_{i=1}^{k} 1 - EPP_{A \rightarrow PO_i}$$

where k is the number of primary outputs. It is noted that $EPP_{c=1}(A)$ computes the EPP of node A at the first clock cycle. The transient error, however, can be captured in flip-flops and propagated to primary outputs in the next clock cycles. To compute EPP of a node in the next clock cycles (c>1), the same error propagation rules can be repeated in the next cycles. It is further noted that in multiple cycle simulations (c>1), the transient error disappears from the original error site. In this case, flip-flops are considered as possible error sites. Using the error propagation rules $EPP_{c=2}(A)$, $EPP_{c=3}(A)$, $EPP_{c=4}(A)$ are computed accordingly. Experimentation has shown that $EPP_{c=x}(A)$ for x>4 becomes very close to 0, such that these probability values can be ignored without sacrificing any accuracy. Finally, the overall EPP value of a node A is can be calculated according to the following equation:

$EPP(A) = EPP_{c=1}(A) + (1-EPP_{c=1}(A)) \times EPP_{c=2}(A) + (1-EPP_{c=1}(A)) \times (1-EPP_{c=2}(A)) \times EPP_{c=3}(A) + (1-EPP_{c=1}(A)) \times (1-EPP_{c=2}(A)) \times (1-EPP_{c=3}(A)) \times EPP_{c=4}(A)$ As noted above, the disclosed systems and methods may be advantageously applied to any living or non-living molecular network, including molecular networks of humans, animals, plants, etc. In addition, the network may take a variety of forms, e.g., the network may be a signaling network, genetic network, metabolic network or other networks, as will be readily apparent to persons skilled in the art based on the disclosure/exemplary embodiments provided herein.

As also disclosed herein, a host of algorithms may be used to model the feedback paths, find the feedback paths, and calculate the vulnerability levels of the nodes in a network of interest, including without limitation to the exemplary algorithms disclosed herein. In addition, although the disclosed systems/methods may be implemented with binary logic, implementations may be easily implemented using a multiple-valued logic model. For example and as noted herein, rather than modeling the activity of a molecule by the two states of "active" and "inactive," the disclosed system/method may model the molecule as "inactive," "active" and "hyperactive." Thus, in this example, ternary logic is used to model a molecular network. The disclosed system/method may also use fuzzy logic to model a molecular network. Regardless of the logic regimen employed, once the circuit equivalent of a molecular network is built based on the chosen logic, the disclosed system/method may be used to identify one or more vulnerable molecules.

Exemplary fault models used to model dysfunctional (faulty) molecules may be "stuck-at-0" and "stuck-at-1" models. However, as noted herein, alternative fault models may be used to describe dysfunctional molecules in different ways, as will be readily apparent to persons skilled in the art, without departing from the spirit or scope of the present disclosure. Based on the selected fault model, the disclosed system facilitates advantageous vulnerability assessments for molecular networks, as described herein.

Of further note, beyond the "digital" circuit representations of molecular networks used in the exemplary implementations provided herein, the disclosed systems/method may be implemented as an "analog" circuit representation for modeling a molecular network. In analog-based implementations, the disclosed system/method may employ "analog fault models" and "analog test" or "analog fault identification/detection/diagnosis" methods, to identify/find one or more vulnerable molecules. From a broader perspective, a molecular network may be viewed as a dynamical system. Then, for fault assessment, various methods that have been developed for dynamical systems may be employed (see, e.g., Chen, J. and Patton, R. J., "Robust Model-Based Fault Diagnosis for Dynamic Systems," Kluwer (1999); Chiang, L. H., Russell, E. L. and Braatz, R. D., "Fault Detection and Diagnosis in Industrial Systems," Springer (2001); Gertler, J. J., "Fault Detection and Diagnosis in Engineering Systems," Marcel Dekker (1998); Kobricz, J., Koscielny, J. M., Kowalczuk, Z. and Cholewa, W., Eds., "Fault Diagnosis: Models, Artificial Intelligence, Applications," Springer (2004); and Patton, R. J., Frank, P. M. and Clark, R. N., Eds., "Issues of Fault Diagnosis for Dynamic Systems," Springer (2000)).

Still further, artificial intelligence (AI) methods may be used for fault or reliability analysis of industrial processes (Kobricz, J., Koscielny, J. M., Kowalczuk, Z. and Cholewa, W., Eds., "Fault Diagnosis: Models, Artificial Intelligence, Applications," Springer (2004)). The disclosed systems and methods that conceptualize a disorder at the molecular level as a faulty system permit the use of such AI approaches to find key/critical/vulnerable molecules.

Exemplary systems according to the present disclosure include a processor in communication with computer memory, and a computer program that is adapted to interact with the computer memory (e.g., is stored thereon) and may be run/operated by the processor. Exemplary computer programs according to the present disclosure are adapted to:

a. a computer program interacting with the computer memory and operative on the processor, said computer program being adapted to:
  i. access specified nodes for the biological network, including one or more input nodes and one or more output nodes; identified interactions between specified nodes; equations for the biological system derived using the identified interactions; and a system representation constructed of the derived equations;
  ii. identify feedback paths for the system representation; and
  iii. apply a fault diagnosis technique to determine vulnerability level for at least one specified node.

Selection of appropriate hardware and hardware/software configurations for implementation of the disclosed system are well within the skill of persons in the art.

In general, the systems and methods disclosed herein advantageously provide a new framework in systems biology that can potentially have a high impact on several areas of biology and technology. This cross-disciplinary approach advantageously utilizes circuit analysis techniques to identify and isolate the vulnerable molecules that play crucial roles in the dysfunction of molecular networks. The systems and methods applied to the exemplary p53, caspase3-FKHR and CREB signaling pathways herein proved to be biologically relevant, thus demonstrating the reliability and efficacy of the disclosed approach.

Using the system and methods of the invention, the inventors have identified molecular entities in the regulation of CREB (cAMP response element-binding) that were previously unknown. More specifically, the inventors have identified $G_{\alpha 1}$ and P/Q type Calcium Channel as novel regulators of CREB. Notably, the system and method of the invention also identified a number of molecular vulnerabilities that have been previously shown to be the main regulators of CREB, including, cAMP, AC1, AC2, AC5 and PKA. The identification of entities that have been shown, through empirical evidence, to regulate CREB shows the predictive accuracy of the instant invention.

CREB proteins are transcription factors which bind to certain DNA sequences called cAMP response elements (CREs) and thereby increase or decrease the transcription of certain genes. CREB is highly related (in structure and function) to CREM (cAMP response element modulator) and ATF-1 (activating transcription factor-1) proteins. Activation of CREB occurs in response to external stimuli, for example, the activation of a membrane surface receptor. The activated receptor, in turn, leads to the activation of effector molecules leading to the production of cyclic-AMP or Ca2+ release, which leads to the activation of a protein kinase. This protein kinase translocates to the cell nucleus, where it activates the CREB protein. The activated CREB protein then binds to a CRE region, and is then bound by a CREB binding protein (CBP) which coactivates it, allowing it to switch certain genes on or off. The DNA binding of CREB is mediated via its basic leucine zipper domain.

CREB proteins play a major role in regulating gene expression in neurons, and are believed to be involved in long-term potentiation (i.e., long-term memories). CREB is also important for the survival of neurons, as shown in genetically engineered mice, where CREB and CREM were deleted in the brain. If CREB is lost in the whole developing mouse embryo, the mice die immediately after birth, again highlighting the critical role of CREB in promoting survival. Moreover, disturbance of CREB function in brain can contribute to the development and progression of Huntington's Disease, Alzheimer's, Rubinstein-Taybi syndrome, cancer, as well as other neuropathologies such as schizophrenia, anxiety disorders as well as the other psychiatric disorders.

For a more detailed discussion of CREB physiology, see: Barco A, Bailey C, Kandel E (2006), "Common molecular mechanisms in explicit and implicit memory," *J. Neurochem.* 97 (6): 1520-33; Conkright M, Montminy M (2005), "CREB: the unindicted cancer co-conspirator," *Trends Cell Biol.* 15 (9): 457-9; Mantamadiotis T., et al., (2002), "Disruption of CREB function in brain leads to neurodegeneration," *Nat. Genet.* 31 (1): 47-54; Mayr B, Montminy M (2001), "Transcriptional regulation by the phosphorylation-dependent factor CREB," *Nat. Rev. Mol. Cell Biol.* 2 (8): 599-609; Yin J., et al., "CREB as a memory modulator: induced expression of a dCREB2 activator isoform enhances long-term memory in *Drosophila*," *Cell* 81 (1): 107-15, which are incorporated herein by reference in their entirety for all purposes.

As indicated previously, one of the molecules that have been identified using the system and methods of the invention as being a vulnerable molecule in the dysregulation of CREB is the guanine-nucleotide binding protein (i.e., G-protein), $G_{\alpha i}$. The dysfunction of $G_{\alpha i}$ has not previously been implicated in the aberrant modulation of CREB activity. G proteins, are a family of heterotrimeric proteins involved in second messenger cascades.

Heterotrimeric G-proteins are activated by G protein-coupled receptors (GPCRs) and made up of alpha ($\alpha$), beta ($\beta$), and gamma ($\gamma$) subunits. G-proteins function as molecular switches, alternating between an inactive, guanosine diphosphate (GDP) bound state, and an active, guanosine triphosphate (GTP) bound state. Receptor-activated G-proteins are bound to the inside surface of the cell membrane. They consist of the $G_\alpha$ and the tightly-associated $G_{\beta\gamma}$ subunits. At the present time, four main families exist for $G_\alpha$ subunits: $G_{\alpha s}$, $G_{\alpha i}$, $G_{\alpha q/11}$, and $G_{\alpha 12/13}$. These groups differ primarily in effector recognition, but share a similar mechanism of activation. When a ligand activates the GPCR, it induces a conformation change in the receptor that allows the receptor to function as a guanine nucleotide exchange factor (GEF) that exchanges GTP for GDP on the $G_\alpha$ subunit. In the traditional view of heterotrimeric protein activation, this exchange triggers the dissociation of the $G_\alpha$ subunit from the $G_{\beta\gamma}$ dimer and the receptor. However, certain studies also suggest that G-proteins function through molecular rearrangement, reorganization, and pre-complexing of effector molecules. Furthermore, both $G_\alpha$-GTP and $G_{\beta\gamma}$ can activate different signaling cascades (or second messenger pathways) and effector proteins, while the receptor is able to activate the next G protein. Once in its active state, the $G_\alpha$ subunit will eventually hydrolyze the attached GTP to GDP by its inherent enzymatic activity, allowing it to re-associate with $G_{\beta\gamma}$ and starting a new cycle.

The class of G-proteins known as $G_{\alpha i}$ are known to inhibit the production of cAMP through an antagonistic interaction with the enzyme, adenylate cyclase. $G_{\alpha i}$ is known to complex with several GPCRs including the 5-HT (serotonin) Receptor type 1, Adenosine Receptor A1 and A3, and Prostaglandin Receptors. Interestingly, the $G_{\beta\gamma}$ subunit of G-proteins are also known to couple to L-type calcium channels, affecting their voltage activation/inactivation, single-channel conductance, and/or open probability.

Fault diagnosis engineering analysis of the CREB pathway performed according to the methods described herein, identified $G_{\alpha i}$ as a highly vulnerable molecule in the CREB pathway. To date, there have been no reports showing that $G_{\alpha i}$ can modulate the activity of CREB. As such, the inventors contemplate methods of modulation of $G_{\alpha i}$ activity, either directly or indirectly, for the treatment or prevention of neuropathological disorders, for example, memory loss, Parkinson's, Alzheimer's, Huntington's disease, schizophrenia, dementia and other neurodegenerative and psychiatric brain disorders manifested by memory dysfunction. In addition, the inventors contemplate methods for the activation of pathways which antagonize $G_{\alpha i}$ activity, for example, the activation of $G_{\alpha s}$, or the activation of adenylate cyclase as a means of treating CREB-related disorders. Moreover, the inventors also contemplate methods in which the activity of $G_{\alpha i}$ is measured as a means for identifying and/or screening potential therapeutic compounds. Furthermore, the inventors also contemplate the use of $G_{\alpha i}$ activity, gene or gene expression as a means of detecting or diagnosing a disease state, for example, the presence, absence or severity; or determining an individual's predisposition to developing a neuropathological disease related to CREB dysfunction.

Fault diagnosis engineering analysis of the CREB pathway performed according to the methods of the invention have also identified for the first time that the P/Q type calcium channel is a highly vulnerable molecule in the CREB pathway. This means that the functionality of CREB is closely correlated to the activity level of P/Q type calcium channel. Therefore, the system and methods of the invention have also implicated, for the first time, the dysfunction of the P/Q Calcium Channel in CREB-related neuropathologies. The P/Q channel is an L-type, voltage-gated calcium channel, and is the main channel involved in nerve evoked neurotransmitter release at neuromuscular junctions (NMJs) and many central nervous system synapses. The P/Q channel becomes activated (i.e., opens), in response to membrane depolarization, for example, from the binding of a neurotransmitter to its receptor. Once activated, the P/Q channel allows calcium ions to enter the synapse. Calcium also acts as a second messenger, triggering neurotransmitter release/uptake as well as inducing changes in gene expression.

As indicated above, it has been shown that G-protein beta-gamma subunits can interact with L-type calcium channels. Therefore, is remains possible that $G_{\alpha i}$ dysfunction is compounded by inducing aberrant regulation of P/Q channels, which may further lead to dysfunction of CREB. As such, the inventors contemplate additional methods of modulation of P/Q channel activity, either directly or indirectly, for the treatment or prevention of neuropathological disorders, for example, memory loss, Parkinson's, Alzheimer's, Huntington's disease, schizophrenia, dementia, and psychiatric or neurological conditions manifested by memory dysfunction. Moreover, the inventors also contemplate methods in which the activity of the P/Q channel (i.e., open probability, activation/inactivation kinetics, channel current, conductance, and the like) is measured as a means for identifying and/or screening potential therapeutic compounds. Furthermore, the inventors also contemplate the use of the P/Q channel activity, gene or gene expression as a means of detecting or diagnosing a disease state, for example, the presence, absence or severity; or determining an individual's predisposition to developing a neuropathological disease related to CREB dysfunction.

Furthermore, the inventors contemplate methods in which agonists or antagonists of the P/Q channel and $G_{\alpha i}$ are administered simultaneously for the treatment and/or prevention of neuropathological disease related to CREB dysfunction. Many P/Q channel and $G_{\alpha i}$ agonists and antagonists are currently available (e.g., omega-conotoxind, omega-agatoxin, verapamil, diltiazem, DHP, roscovitine, nifedipine, atrophic, Bay K 8644; NEM, forskolin, cholera toxin, pertussis toxin, respectively), and methods for their use are either known or readily ascertainable by those of skill in the art without undue experimentation. Similarly, methods and assays for screening a library of compounds for their ability to activate or inhibit P/Q channel activity and/or $G_{\alpha i}$ activity are widely known, and therefore, the identification of additional agonists/antagonists requires only routine experimentation by those of skill in the art in view of the instant teachings.

As described herein, an additional advantage of the instant methods is the biological application of fault diagnosis engineering for identification of critical molecules in complex signaling pathways. As such, the present methods provide for the identification of alternative, safe therapeutic routes and targets. For example, vulnerability analysis of the CREB pathway shows that CREB function is as vulnerable to the dysfunction of PKA as to the dysfunction of the P/Q channel and $G_{\alpha i}$ activity. Obviously it is impossible to target PKA for treatment of disorders related to the CREB function due to the fact that PKA function is essential for overall cellular function and viability. However, as described herein, there are alternative molecules such as the P/Q channel and $G_{\alpha 1}$ that can be targeted, and therefore, be as effective as targeting PKA. In addition, the vulnerability assessment tool is also able to identify alternative targets for significantly modulating the activity of the output node that are safer and easier to target, and therefore, will reduce the likelihood of toxicity or undesirable side effects.

As noted herein, a variety of techniques and methods may be used to model and analyze biological systems as digital circuits according to the present disclosure. For example, the present disclosure is expressly not limited to fault analysis using the EPP method described herein. Furthermore, it is expressly noted that the systems and methods disclosed herein are not limited to the exemplary algorithms used in identifying and modeling feedback paths for a target system or those used in calculating vulnerability levels. The application of the systems and methods disclosed herein has the potential to improve biological understanding of the cellular-molecular system, from its very basic physiological condition to disease development, and ultimately to drug discovery.

Although the present disclosure has been described with reference to exemplary embodiments and implementations thereof, the present disclosure is not to be limited by or to such disclosed embodiments and/or implementations. Rather, the disclosed fault diagnosis methods have wide ranging applications, and are susceptible to many variations, modifications and/or enhancements without departing from the spirit or scope hereof. The present disclosure expressly encompasses all such variations, modifications and/or enhancements.

REFERENCES

Asadi, H., Tahoori, M. B. (2005) An Accurate SER Estimation Method Based on Propagation Probability, *IEEE Design and Test Automation in Europe*, 306-307.

Asadi, H., Tahoori, M. B. (2005) An analytical approach for soft error rate estimation in digital circuits, *IEEE International Conference on Circuits and Systems*, 2991-2994.

Asadi, H., Tahoori, M. B. (2005) Soft error modeling and protection for sequential elements, *IEEE International Symposium on Defect and Fault Tolerance of VLSI*, 463-474.

Bajic, V. B. and Wee, T. T., Eds. (2005) *Information Processing and Living Systems*, Imperial College Press.

Blain, S. W. & Massague J. Breast cancer banishes p27 from nucleus. *Nat. Med.* 8, 1076-1078 (2002).

Boronenkov, I. V. & Anderson, R. A. The sequence of phosphatidylinositol-4-phosphate 5-kinase defines a novel family of lipid kinases. *J. Biol. Chem.* 270, 2881 (1995).

Bower, J. M. and Bolouri, H., Eds. (2001) *Computational Modeling of Genetic and Biochemical Networks*, MIT Press.

Brazil, D. P., Yang, Z. Z., and Hemmings, B. A. (2004) Advances in protein kinase B signaling: AKTion on multiple fronts. *Trends Biochem. Sci,* 29, 233-242 (2004).

Bushnell, M. L. and Agarwal, V. D. (2000) *Essentials of Electronic Testing for Digital, Memory and Mixed-Signal VLSI Circuits*, Kluwer Academic Press.

Cardone, M. H. et al. Regulation of cell death protease caspase-9 by phosphorylation. *Science.* 282, 1318 (1998).

Chen, H. K. et al. Interaction of AKT-phosphorylated ataxin-1 with 14-3-3 mediates neurodegeneration in spinocerebellar ataxia type 1. *Cell* 113, 457-468 (2003).

Colin, E. et al. AKT is altered in an animal model of Huntington's disease and in patients. *Eur. J. Neurosci.* 21, 1478-1488 (2005).

Cormen, T. H. et al., Introduction to Algorithms (MIT Press & McGraw-Hill, ed. 2, 2001).

De Waard, M. et al. Direct binding of G-protein betagamma complex to voltage-dependent calcium channels. *Nature.* 385, 446 (1997).

Delcommenne, M. et al. Phosphoinositide-3-OH kinase-dependent regulation of glycogen synthase kinase 3 and protein kinase B/AKT by the integrin-linked kinase. *Proc. Natl. Acad. Sci. U.S.A.* 95, 11211 (1998).

De Vivo, M. & Maayani, S. Characterization of the 5-hydroxytryptamine 1a receptor-mediated inhibition of forskolin-stimulated adenylate cyclase activity in guinea pig and rat hippocampal membranes. *J. Pharmacol. Exp. Ther.* 238, 248 (1986)

Emamian E. S. et al. Serine 776 of ataxin-1 is critical for polyglutamine-induced disease in SCA1 transgenic mice. *Neuron* 38, 375-387 (2003).

Emamian, et al. Convergent evidence for impaired AKT1-GSK3beta signaling in schizophrenia. *Nat. Genetics* 36, 131-137 (2004).

Finkel, T. and Gutkind, J. S., Eds. (2003) *Signal Transduction and Human Disease*, Wiley.

Gomperts, B. D., Kramer, I. M. and Tatham, P. E. R. (2002) *Signal Transduction*, Academic Press.

Griffin, R. J. et al. Activation of AKT/PKB, increased phosphorylation of AKT substrates and loss and altered distribution of AKT and PTEN are features of Alzheimer's disease pathology. *J. Neurochem.* 93:105-117 (2005).

Husmeier, D., Dybowski, R. and Roberts, S., Eds., (2005) *Probabilistic Modeling in Bioinformatics and Medical Informatics*, Springer.

Ideker, T. and Lauffenburger, D. (2003) Building with a scaffold: Emerging strategies for high- to low-level cellular modeling, *Trends in Biotechnology,* 21, 255-62.

Janes, K. A. et al., *Cell* 124, 1225 (2006).

Janes, K. A. et al., *Mol. Cell. Proteomics* 2, 463 (2003).

Kandel, E. R. The molecular biology of memory storage: a dialogue between genes and synapses. *Science* 294, 1030-1038 (2001).

Kaspar, B. K. et al. Retrograde viral delivery of IGF-1 prolongs survival in a mouse ALS model. *Science* 301, 839-842 (2003).

Klipp, E., Herwig, R., Kowald, A., Wierling, C. and Lehrach, H. (2005) *System Biology in Practice*, Wiley.

Levine, A. J. et al. The P53 pathway: what questions remain to be explored? *Cell Death Differ.* 13, 1027-1036 (2006).

Liang, J. et al. PKB/AKT phosphorylates p27, impairs nuclear import of p27 and opposes p27-mediated G1 arrest. *Nat. Med.* 8, 1153-1160 (2002).

Luo, J. et al., *Cancer Cell* 4, 257 (2003).

Ma'ayan, A. et al., *Science* 309, 1078 (2005).

McCluskey, E. J. et al., Logic Design Principles (Prentice-Hall, 1986).

Papin, J. A., Hunter, T., Palsson, B. O. and Subramanian, S. (2005) Reconstruction of cellular signaling networks and analysis of their properties, *Nature Reviews-Molecular Cell Biology*, 6, 99-111.

Saez-Rodriguez, J. Kremling, A., Conzelmann, H., Bettenbrock, K. and Gilles, E. D. (2004) Modular analysis of signal transduction networks, *IEEE Control Systems Mag.*, 35-52.

Saudou, F. et al. Huntingtin acts in the nucleus to induce apoptosis but death does not correlate with the formation of intranuclear inclusions. *Cell* 95, 55-66 (1998).

The invention claimed is:

1. A method for determining vulnerabilities of a molecular network of a biological system, the method comprising:
   (a) converting the molecular network of the biological system to a plurality of nodes including at least one input node, at least one output node, and at least one intermediate node between said input and output nodes, wherein each said node is a representation of a molecular entity within said biological system;
   (b) identifying interactions between said nodes using relevant biological, physical or biochemical information;
   (c) transforming the interactions identified in step (b) into at least one mathematical equation;
   (d) assigning at least one fault model to said at least one mathematical equation;
   (e) assigning a numerical value to at least one of said node(s) wherein said value indicates the vulnerability level of at least one of said node(s) for at least one pathological condition, by computing the response of at least one intermediate or output node mentioned in step (a);
   (f) selecting at least one node having a computed vulnerability level according to step (e), as a target node and,
   (g) treating said pathological condition by using said determined target node for drug development.

2. The method of claim 1, wherein the input node(s) is a molecular entity selected from the group consisting of biological ligands, cell receptors and secondary messengers.

3. The method of claim 1, wherein the output node(s) comprises at least one transcription factor.

4. The method of claim 1, wherein the identified interactions of step (b) include at least (i) a stimulatory interaction, (ii) an inhibitory interaction or both.

5. The method of claim 1, wherein a node affected by at least one inhibitory input node(s) is considered inactive only if at least one of the inhibitory input nodes is active, and a node affected by at least one stimulatory input node(s) and no inhibitory input node is considered active only if at least one of the stimulatory node(s) is active.

6. The method of claim 1, wherein the mathematical equation is at least one logic equation.

7. The method of claim 6, wherein said at least logic equation is a binary logic equation.

8. The method of claim 1, wherein the mathematical equation is converted into a circuit.

9. The method of claim 8, wherein the circuit is represented digitally.

10. The method of claim 9, wherein the digitally represented circuit is constructed using combinations of AND, OR, NOT, and BUFFER logic operations.

11. The method of claim 1, further comprising identifying feedback paths in said network.

12. The method of claim 11, wherein at least one flip-flop is inserted in at least one feedback path.

13. The method of claim 1, further wherein computing the response includes calculation of error propagation probability.

14. The method of claim 13, wherein said error probability is the probability of having unexpected output node(s) response(s), if said node(s) is faulty.

15. The method of claim 14, wherein input signal(s) are uncorrelated.

16. The method of claim 14, wherein input signal(s) are equiprobable.

17. The method of claim 14, wherein input signal(s) are uncorrelated and equiprobable.

18. The method of claim 14, wherein input signal(s) are uncorrelated and equiprobable, and have the same probability of 0.5 to be active or inactive.

19. The method of claim 1, further wherein computing the response includes the steps of
   (a) extracting all on-path signals and gates to every reachable primary output;
   (b) prioritizing signals on the paths based on their distance level; and
   (c) traversing the paths and applying propagation rules to compute the probability for each one path node.

20. The method of claim 19, wherein the on-path signals and gates are extracted using a forward depth-first search algorithm.

21. The method of claim 19, wherein the signals on the paths are prioritized using a topological sorting algorithm and wherein the paths are traversed in a topological order.

22. A computer readable program for identifying the dysfunction of at least one molecule, within in a biological network according to process of claim 1 adapted to:
   (i) access specified nodes for the biological network, including at least one input node(s) and at least one output node(s) and at least one intermediate node(s) between said input and said output node(s);
   (ii) access interactions among said specified nodes;
   (iii) compute equations; and
   (iv) apply a fault diagnosis technique to determine vulnerability level for at least one of said specified nodes, wherein the fault diagnosis technique includes the steps of
   (a) extracting all on-path signals and gates to every reachable primary output;
   (b) prioritizing signals on the paths based on their distance level; and
   (c) traversing the paths and applying propagation rules to compute the probability for each on-path node.

23. The system of claim 22, wherein the on-path signals and gates are extracted using a forward depth-first search algorithm.

24. The system of claim 22, wherein the signals on the paths are prioritized using a topological sorting algorithm and wherein the paths are traversed in a topological order.

25. The method of claim 1, wherein said pathological condition is selected from the group consisting of cancer, neurological and psychiatric disorders, metabolic disorders, autoimmune diseases, rheumatological disorders, hematological disorders, cardiovascular diseases, dermatological diseases, and genetic abnormalities.

26. The method of claim 25, wherein said pathological condition is selected from the group consisting of breast cancer, prostate cancer, lung cancer, gastrointestinal cancer, pancreatic cancer, hepatocellular carcinoma, thyroid cancer, glioblastoma, gliomas, Alzheimer disease, schizophrenia, ataxia, anemia, chorea, Huntington's disease, neurofibromatosis, and polycystic kidney disease.

27. The method of claim 1, wherein the said at least one fault model(s) in step (d) represents mutations or other structural/functional abnormalities in at least one molecule.

28. The method of claim 1, wherein the said at least one fault model(s) in step (d) indicates that the status or state or numerical value of at least one mathematical variable in at least one of the said mathematical equation(s) does not change, temporarily or permanently, due to a faulty condition of the node that is represented by the said mathematical variable.

29. The method of claim 1, wherein the said at least one fault model(s) in step (d) indicates that the binary status or state or numerical value of at least one mathematical variable in at least one of the said mathematical equation(s) does not change, temporarily or permanently, due to a faulty condition of the node that is represented by the said mathematical variable.

30. The method of claim 1, wherein said treating step (g) further comprising pharmacologically activating, antagonizing, regulating, inhibiting, increasing or decreasing expression level of the corresponding molecule to said target node of step (f).

31. A system for identifying molecular vulnerabilities in a biological network, the system comprising:
(1) a processor in communication with computer memory, and
(2) a computer program interacting with the computer memory and operative on the processor, said computer program being adapted to perform the following steps:
(a) converting the molecular network of the biological system to a plurality of nodes including at least one input node, at least one output node, and at least one intermediate node between said input and output nodes, wherein each said node is a representation of a molecular entity within said biological system;
(b) identifying interactions between said nodes using relevant biological, physical or biochemical information;
(c) transforming the interactions identified in step (b) into at least one mathematical equation;
(d) assigning at least one fault model to said at least one mathematical equation to determine vulnerability level of at least one specified node;
(e) assigning a numerical value to at least one of said node(s) wherein said value indicates the vulnerability level of at least one of said node(s) for at least one pathological condition, by computing the response of at least one intermediate or output node mentioned in step (a);
(f) reporting at least one node having a computed vulnerability level according to step (e), as a target node, and
(g) treating said pathological condition by using said determined target node for drug development.

32. The system of claim 31, wherein the input node is a molecular entity selected from the group consisting of biological ligands, cell receptors and secondary messengers.

33. The system of claim 31, wherein the output node is a transcription factor.

34. The system of claim 31, wherein the identified interactions of step (b) include at least (i) a stimulatory interaction, or (ii) an inhibitory interaction or both.

35. The system of claim 31, wherein the computer program is adapted to identify:
(i) a node affected by at least one inhibitory input node(s) as inactive only if at least one of the inhibitory input nodes is active, and
(ii) a node affected by at least one stimulatory input node(s) and no inhibitory input node as active only if at least one of stimulatory nodes is active.

36. The system of claim 31, wherein the mathematical equation(s) is at least one logic equation(s).

37. The system of claim 36, wherein said at least one logic equation is a binary logic equation.

38. The system of claim 31, wherein the mathematical equation is converted into a circuit.

39. The system of claim 38, wherein the circuit is a digital circuit.

40. The system of claim 39, wherein the-digital circuit is constructed using combinations of AND, OR, NOT, and BUFFER logic operations.

41. The system of claim 40, wherein the computer program further identifies feedback paths.

42. The system of claim 41, wherein at least one flip-flop is inserted in at least one feedback path.

43. The system of claim 31, further wherein the computing the response technique includes calculation of error propagation probability.

44. The system of claim 43, wherein said error probability is the probability of having unexpected output node(s) response(s), if said node(s) is faulty.

45. The system of claim 44, wherein input signal(s) are uncorrelated.

46. The system of claim 44, wherein input signal(s) are equiprobable.

47. The system of claim 44, wherein input signal(s) are uncorrelated and equiprobable.

48. The system of claim 44, wherein input signal(s) are uncorrelated and equiprobable, and have the same probability of 0.5 to be active or inactive.

49. The system of claim 31, wherein the vulnerability measurement of the network is associated with at least one pathological condition.

50. The system of claim 49, wherein said pathological condition is selected from the group consisting of cancer, neurological and psychiatric disorders, metabolic disorders, autoimmune diseases, rheumatological disorders, hematological disorders, cardiovascular diseases, dermatological diseases, and genetic abnormalities.

51. The system of claim 50, wherein said pathological condition is selected from the group consisting of breast cancer, prostate cancer, lung cancer, gastrointestinal cancer, pancreatic cancer, hepatocellular carcinoma, thyroid cancer, glioblastoma, gliomas, Alzheimer disease, schizophrenia, ataxia, anemia, chorea, Huntington's disease, neurofibromatosis, and polycystic kidney disease.

52. The system of claim 31, wherein the said at least one fault model(s) in step (d) represents mutations or other structural/functional abnormalities in at least one molecule.

53. The system of claim 31, wherein the said at least one fault model(s) in step (d) indicates that the status or state or numerical value of at least one mathematical variable in at least one of the said mathematical equation(s) does not change, temporarily or permanently, due to a faulty condition of the node that is represented by the said mathematical variable.

54. The system of claim 31, wherein the said at least one fault model(s) in step (d) indicates that the binary status or state or numerical value of at least one mathematical variable in at least one of the said mathematical equation(s) does not change, temporarily or permanently, due to a faulty condition of the node that is represented by the said mathematical variable.

55. The system of claim 31, wherein said treatment option further comprising pharmacologically activating, antagonizing, regulating, inhibiting, increasing or decreasing expression level of the corresponding molecule to said target node of step (f).

* * * * *